(12) United States Patent
Blommel et al.

(10) Patent No.: US 12,017,990 B2
(45) Date of Patent: Jun. 25, 2024

(54) SYSTEMS AND METHODS FOR PRODUCING HIGH PURITY AROMATICS FROM A MIXED AROMATIC FEED STREAM

(71) Applicant: Virent, Inc., Madison, WI (US)

(72) Inventors: Paul G. Blommel, Oregon, WI (US); Matthew Van Straten, Madison, WI (US); Brice Dally, Madison, WI (US)

(73) Assignee: VIRENT, INC., Madison, WI (US)

( * ) Notice: Subject to any disclaimer, the term of this patent is extended or adjusted under 35 U.S.C. 154(b) by 0 days.

(21) Appl. No.: 17/965,614

(22) Filed: Oct. 13, 2022

(65) Prior Publication Data

US 2023/0125062 A1 Apr. 20, 2023

Related U.S. Application Data

(60) Provisional application No. 63/255,812, filed on Oct. 14, 2021.

(51) Int. Cl.
| | |
|---|---|
| *C07C 6/12* | (2006.01) |
| *C07C 7/00* | (2006.01) |
| *C07C 7/05* | (2006.01) |
| *C07C 7/09* | (2006.01) |
| *C10G 3/00* | (2006.01) |

(52) U.S. Cl.
CPC ................ *C07C 7/005* (2013.01); *C07C 6/12* (2013.01); *C07C 7/05* (2013.01); *C07C 7/09* (2013.01)

(58) Field of Classification Search
CPC .. C07C 7/005; C07C 7/05; C07C 7/09; C07C 6/12; C07C 7/12; C07C 7/14; C07C 6/126; C07C 5/2732; C07C 2529/40; C10G 3/42; C10G 2300/1096; C10G 45/62; C10G 45/64; C10G 47/18; C10G 47/20; C10G 2400/30
See application file for complete search history.

(56) References Cited

U.S. PATENT DOCUMENTS

| | | |
|---|---|---|
| 3,702,886 A | 11/1972 | Argauer et al. |
| 3,709,979 A | 1/1973 | Chu et al. |
| 3,832,449 A | 8/1974 | Rosinski et al. |
| 3,948,758 A | 4/1976 | Bonacci et al. |
| 4,016,245 A | 4/1977 | Plank et al. |
| 4,041,091 A * | 8/1977 | Henry ........................ C07C 7/04 203/25 |

(Continued)

FOREIGN PATENT DOCUMENTS

EP 3015445 A1 4/2016

OTHER PUBLICATIONS

Tsai, T. C., Liu, S. B., & Wang, I. (1999). Disproportionation and transalkylation of alkylbenzenes over zeolite catalysts. Applied Catalysis A: General, 181(2), 355-398.

(Continued)

*Primary Examiner* — In Suk C Bullock
*Assistant Examiner* — Jason Y Chong
(74) *Attorney, Agent, or Firm* — Quarles & Brady LLP

(57) ABSTRACT

The present disclosure provides systems and methods for producing aromatic compounds in high yield from a mixed aromatic feed stream. Also disclosed are systems and methods for producing aromatic compounds in high yield from oxygenated hydrocarbons such as carbohydrates, sugars, sugar alcohols, sugar degradation products, and the like.

15 Claims, 2 Drawing Sheets

(56) References Cited

U.S. PATENT DOCUMENTS

| | | |
|---|---|---|
| 4,076,842 A | 2/1978 | Plank et al. |
| 4,100,262 A | 7/1978 | Pelrine |
| 4,107,195 A | 8/1978 | Rollmann |
| 4,139,600 A | 2/1979 | Rollmann et al. |
| 4,375,573 A | 3/1983 | Young |
| 5,004,855 A | 4/1991 | Tada et al. |
| 5,019,663 A | 5/1991 | Chou et al. |
| 7,022,888 B2 | 4/2006 | Choudhary et al. |
| 2010/0228066 A1* | 9/2010 | Kong .................... C10G 65/12 585/321 |
| 2012/0053382 A1 | 3/2012 | Wang et al. |
| 2012/0067774 A1 | 3/2012 | Frey et al. |
| 2013/0263498 A1 | 10/2013 | Kania et al. |
| 2014/0349361 A1 | 11/2014 | Blommel et al. |
| 2015/0065768 A1 | 3/2015 | Bresler et al. |
| 2015/0166434 A1 | 6/2015 | Ward |
| 2015/0307412 A1 | 10/2015 | Whitchurch et al. |
| 2017/0044443 A1 | 2/2017 | Blommel et al. |
| 2017/0349508 A1 | 12/2017 | Montalbano et al. |
| 2020/0017773 A1 | 1/2020 | Ramamurthy et al. |
| 2021/0130716 A1 | 5/2021 | Xu et al. |

OTHER PUBLICATIONS

International Search Report and the Written Opinion of the International Searching Authority, or the Declaration, dated May 25, 2023, 31 pages.

\* cited by examiner

SYSTEMS AND METHODS FOR PRODUCING HIGH PURITY AROMATICS FROM A MIXED AROMATIC FEED STREAM

CROSS-REFERENCE TO RELATED APPLICATIONS

This application claims priority to U.S. Provisional Application No. 63/255,812, filed Oct. 14, 2021, the content of which is hereby incorporated by reference in its entirety.

BACKGROUND

Aromatic hydrocarbons, notably benzene, toluene, and xylenes are important industrial commodities used to produce numerous chemicals, fibers, plastics, and polymers, including styrene, phenol, aniline, polyester, and nylon. Typically, such aromatic hydrocarbons are produced from petroleum feedstocks using well-established refining or chemical processes. More recently, there is a growing interest in providing aromatic hydrocarbons from alternative resources, such as biomass, synthesis gases and natural gas.

SUMMARY OF THE INVENTION

In one aspect, the present disclose provides a method for separating an aromatic compound from a mixed aromatic feed stream. The method may comprise (i) contacting a mixed aromatic feed stream comprising $C_{7-10}$ aromatics with an aromatics processing catalyst to produce a product stream, wherein the aromatics processing catalyst comprises a transalkylation catalyst, a dealkylation catalyst, a hydrocracking catalyst, or a combination thereof. The mixed aromatic feed may comprise greater than 1 wt % of non-aromatic components based on the total weight of the mixed aromatic feed stream. The mixed aromatic feed may be substantially free of $C_{12+}$ aromatics. The method may further includes (ii) fractionating the product stream to separate an aromatic compound from the product stream.

In some embodiments, based on the total weight of the mixed aromatic feed stream, the mixed aromatic feed stream may comprise: from 0.1 wt % to 45 wt % olefins; from 0.1 wt % to 25 wt % naphthenes; from 0.1 wt % to 40 wt % naphtheno-olefins; phenols in an amount from 10 ppm to 10 wt %; and/or oxygenates in an amount from 10 ppm to 10 wt %. In some embodiments, the mixed aromatic feed stream has a bromine number of at least 1 mg $Br_2$/g of the mixed aromatic feed to less than 100 mg $Br_2$/g of the mixed aromatic feed. In some embodiments, the mixed aromatic feed steam is substantially free of co-boiling contaminants for benzene, toluene, and a combination thereof. In some embodiments, the mixed aromatic feed stream comprises $C_{9-10}$ aromatics In some embodiments, step (ii) of the present method comprises feeding the product stream comprising $C_8$ aromatics to a first distillation column that fractionates the product stream to separate a $C_{7-}$ stream from a $C_{8+}$ stream. The $C_{7-}$ stream may be fed to a second distillation column that fractionates the $C_{7-}$ stream into a $C_{6-}$ stream and a $C_7$ stream. In some embodiments, at least a portion of the $C_7$ stream is recycled and combined with the mixed aromatic feed stream.

In some embodiments, step (ii) further comprises feeding the $C_{8+}$ stream to a third distillation column that fractionates the $C_{8+}$ stream into a $C_8$ stream and a $C_{9+}$ stream. The $C_8$ stream may comprise the $C_8$ aromatics. The $C_{9+}$ stream may be fed to a fourth distillation column that fractionates the $C_{9+}$ stream into a $C_{9-10}$ stream and a $C_{11+}$ stream. The $C_{9-10}$ stream may be recycled and combined with the mixed aromatic feed stream.

In some embodiments, the present method may further comprise: (iii) subjecting at least a portion of the $C_8$ stream to an isomer-recovery process unit to produce a xylene isomer stream and a raffinate stream comprising non-recovered $C_8$ compounds; and (iv) contacting the raffinate stream with an isomerization catalyst to produce an isomerization product stream. The isomerization product stream may comprise at least one xylene isomer. At least a portion of the isomerization product stream may be combined with the product stream produced from the aromatics processing catalyst in step (i).

In some embodiments, at least a portion of the isomerization product stream is combined with the $C_8$ stream entering the isomer-recovery process unit.

In some embodiments, at least a portion of the $C_{8+}$ stream is combined with the $C_8$ stream entering the isomer-recovery process unit.

In some embodiments, step (ii) of the present method comprises fractionating the product stream to separate a $C_7$ stream, a $C_8$ stream, and a $C_{9-10}$ stream, wherein the $C_8$ stream is fed to the isomer-recovery process unit, the $C_7$ stream is recycled and combined with the mixed aromatic feed stream, and the $C_{9-10}$ stream is recycled and combined with the mixed aromatic feed stream.

In some embodiments, step (ii) comprises fractionating the product stream to separate a $C_7$ stream, a $C_8$ stream, and a $C_{9+}$ stream, wherein the $C_8$ stream is fed to the isomer-recovery process unit, the $C_7$ stream is recycled and combined with the mixed aromatic feed stream, and the $C_{9+}$ stream is recovered as a product.

In some embodiments, the isomer-recovery process unit comprises an adsorption unit or a crystallization unit.

The aromatics processing catalyst of the present method may comprise an acid catalyst. The acid catalyst may comprises aluminosilicates, tungstated aluminosilicates, silica-alumina phosphates, aluminum phosphates, amorphous silica alumina, zirconia, sulfated zirconia, tungstated zirconia, tungsten carbide, molybdenum carbide, titania, acidic alumina, phosphated alumina, tungstated alumina, phosphated silica, tungstated silica, tungstated titania, tungstated phosphate, niobia, sulfated carbons, phosphated carbons, acidic resins, heteropolyacids, tungstated heteropolyacid, inorganic acids, or a combination thereof. The acid catalyst may also comprise a metal, which comprises Cu, Ag, Au, Pt, Ni, Fe, Co, Ru, Rh, Zn, Ga, In, Pd, Ir, Re, Mn, Cr, Mo, W, Sn, Os, alloys, or a combination thereof.

In some embodiments, step (i) of the present method occurs at a temperature from 200° C. to 600° C. In some embodiments, step (i) of the present method occurs at a pressure from 100 psig to 1500 psig. In some embodiments, step (i) of the present method occurs at a weight hourly space velocity (WHSV) from 0.1 to 10 mass feed/mass catalyst/hour. In some embodiments, step (i) of the present method comprises feeding hydrogen in an amount of at least 0.1 mol of hydrogen per mol of mixed aromatic feed, such as at least 1 mol of hydrogen per mol of mixed aromatic feed.

In other aspects, the present disclosure provides a method for producing and separating an aromatic compound from a mixed aromatic feed stream. The method may include (i) contacting an aqueous hydrocarbon feedstock comprising water and one or more oxygenate with a condensation catalyst to produce a condensation product stream comprising $C_{4+}$ compounds. The $C_{4+}$ compounds may comprise, for example, a $C_{4+}$ alcohol, a $C_{4+}$ ketone, a $C_{4+}$ alkane, a $C_{4+}$ alkene, a $C_{5+}$ cycloalkane, a $C_{5+}$ cycloalkene, an aryl, or a fused aryl. The method may further include (ii) fractionating the condensation product stream to generate a light stream and a heavy stream. In some embodiments, the light stream comprises co-boiling non-aromatic contaminants for benzene or toluene, and the heavy stream is substantially free of co-boiling non-aromatic contaminants for benzene or toluene. The method may further include (iii) recycling the light stream to the condensation catalyst and (iv) fractionating the heavy stream into a mixed aromatic feed comprising $C_{7+}$ aromatics. The method may further include (v) contacting the mixed aromatic feed stream with an aromatics processing catalyst to produce a product stream. The aromatics processing catalyst may comprise a transalkylation catalyst, a dealkylation catalyst, a hydrocracking catalyst, or a combination thereof.

In some embodiments, step (iv) further comprises fractionating the mixed aromatic feed comprising $C_{7+}$ aromatics into a $C_{7-10}$ stream and a $C_{11+}$ stream. In some embodiments, step (iv) further comprises fractionating the mixed aromatic feed comprising $C_{7+}$ aromatics into a $C_{9-10}$ stream and a $C_{11+}$ stream. The $C_{7-10}$ stream or the $C_{9-10}$ stream may be contacted with the aromatics processing catalyst.

In some embodiments, step (iv) occurs at a temperature from 200° C. to 600° C. and a pressure from 100 psig to 1500 psig and at a weight hourly space velocity (WHSV) from 0.1 to 10 mass feed/mass catalyst/hour.

In another aspect, the present disclosure provides a method for producing and separating a xylene isomer. The method may comprise (i) contacting a mixed aromatic feed stream comprising $C_{7+}$ aromatics with an aromatics processing catalyst to produce a product stream comprising an increased concentration of $C_8$ aromatics relative to the mixed aromatic feed stream, wherein the aromatics processing catalyst comprises a transalkylation catalyst, a dealkylation catalyst, a hydrocracking catalyst, or a combination thereof. The method may further include (ii) fractionating, using a distillation column, the product stream into a $C_{7-}$ stream and a $C_{8+}$ stream, and (iii) fractionating, using a distillation column, the $C_{8+}$ stream into a $C_8$ stream and a $C_{9+}$ stream. The method may further include (iv) subjecting at least a portion of the $C_8$ stream to an isomer-recovery process unit to produce a xylene isomer stream and a raffinate stream comprising non-recovered $C_8$ compounds, and (v) contacting the raffinate stream with an isomerization catalyst to produce an isomerization product stream, wherein the isomerization product stream comprises at least one xylene isomer. In some embodiments, at least a portion of the $C_{8+}$ stream bypasses the distillation column in step (iii) and is combined with the $C_8$ stream prior to entering the isomer-recovery process unit.

In yet another aspect, the present disclosure provides a method for producing and separating a xylene isomer. The method may include (i) contacting a mixed aromatic feed stream comprising $C_{7+}$ aromatics with an aromatics processing catalyst to produce a product stream comprising an increased concentration of $C_8$ aromatics relative to the mixed aromatic feed stream, wherein the catalyst comprises a transalkylation catalyst, a dealkylation catalyst, a hydrocracking catalyst, or a combination thereof. The method may further include (ii) fractionating, using a distillation column, the product stream into a $C_{7-}$ stream and a $C_{8+}$ stream, and (iii) fractionating, using a distillation column, the $C_{8+}$ stream into a $C_8$ stream and a $C_{9+}$ stream. The method may further include (iv) subjecting at least a portion of the $C_8$ stream to an isomer-recovery process unit to produce a xylene isomer stream and a raffinate stream comprising non-recovered $C_8$ compounds, and (v) contacting the raffinate stream with an isomerization catalyst to produce an isomerization product stream, wherein the isomerization product stream comprises at least one xylene isomer. In some embodiments, at least a portion of the isomerization product stream is combined with the $C_8$ stream prior to entering the isomer-recovery process unit.

The xylene isomer stream may comprise, for example, para-xylene, ortho-xylene, or meta-xylene.

In some embodiments, at least a portion of the $C_{8+}$ stream bypasses the distillation column in step (iii) and is combined with the $C_8$ stream prior to entering the isomer-recovery process unit.

In some embodiments, prior to step (i) the method comprises:
  contacting an aqueous hydrocarbon feedstock comprising water and one or more oxygenate with a condensation catalyst to produce a condensation product stream comprising $C_{4+}$ compounds, wherein the $C_{4+}$ compounds comprise a $C_{4+}$ alcohol, a $C_{4+}$ ketone, a $C_{4+}$ alkane, a $C_{4+}$ alkene, a $C_{5+}$ cycloalkane, a $C_{5+}$ cycloalkene, an aryl, or a fused aryl;
  fractionating the condensation product stream to separate a $C_{6-}$ stream from a $C_{7+}$ stream;
  recycling the $C_{6-}$ stream to the condensation catalyst;
  fractionating the $C_{7+}$ stream into a $C_{7-10}$ stream and a $C_{11+}$ stream, wherein the $C_{7-10}$ stream forms the mixed aromatic feed stream; and
  wherein at least a portion of the $C_{8+}$ stream bypasses the distillation column in step (iii) and is combined with the $C_8$ stream prior to entering the isomer-recovery process unit.

DETAILED DESCRIPTION OF THE INVENTION

Figure 1:
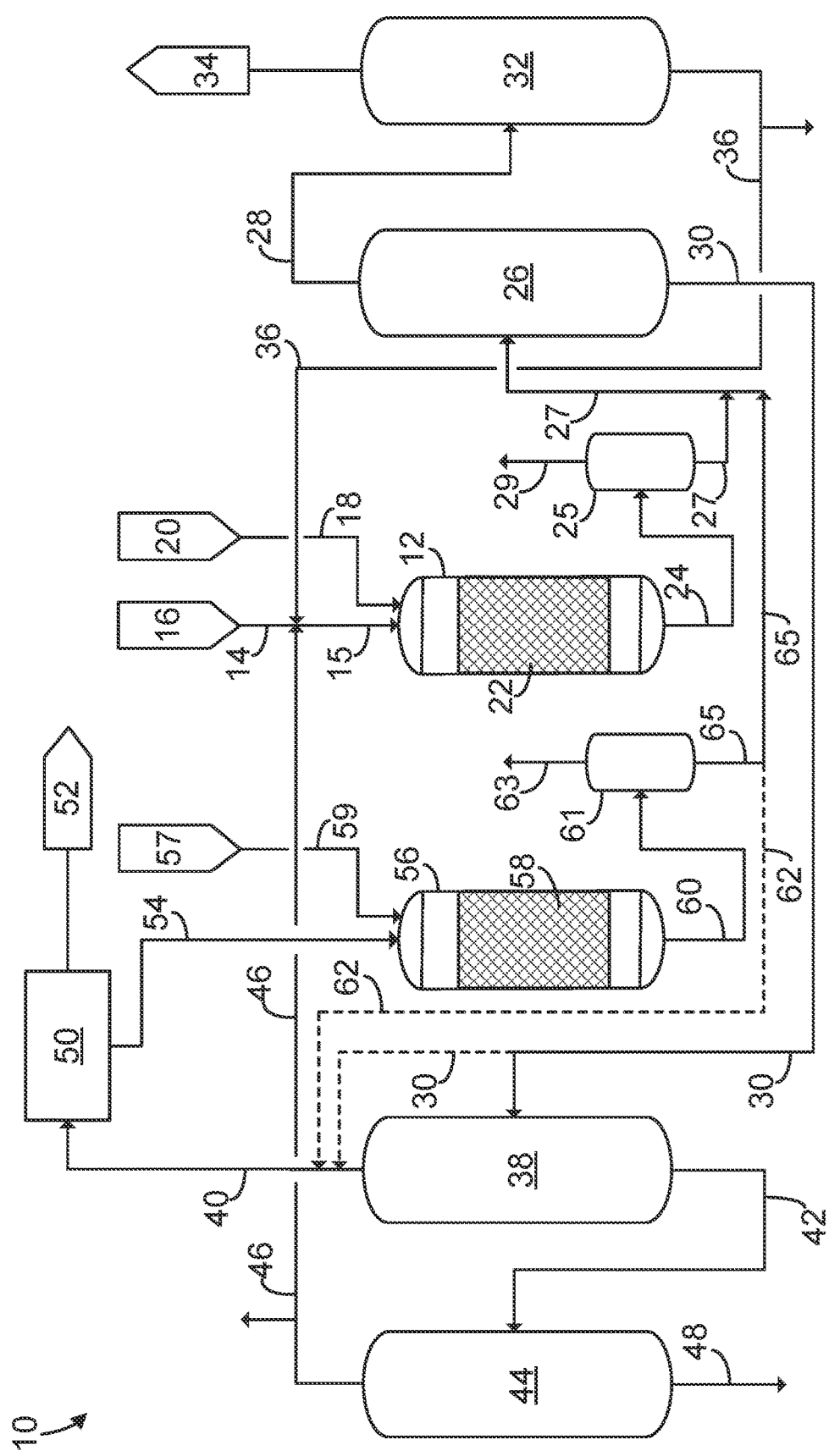
FIG. 1 is a schematic illustration of an aromatics purification system in accordance with some embodiments of the present disclosure.

In order for the present disclosure to be more readily understood, certain terms are first defined below. Additional definitions for the following terms and other terms are set forth throughout the specification.

In this application, unless otherwise clear from context, the term "a" may be understood to mean "at least one." As used in this application, the term "or" may be understood to mean "and/or." In this application, the terms "comprising" and "including" may be understood to encompass itemized components or steps whether presented by themselves or together with one or more additional components or steps. Unless otherwise stated, the terms "about" and "approximately" may be understood to permit standard variation (e.g., ±10%) as would be understood by those of ordinary skill in the art. Where ranges are provided herein, the endpoints are included. As used in this application, the term "comprise" and variations of the term, such as "comprising" and "comprises," are not intended to exclude other additives, components, integers or steps.

Unless defined otherwise, all technical and scientific terms used herein have the same meaning as commonly understood by one of ordinary skill in the art to which the invention pertains. All definitions, as defined and used herein, should be understood to control over dictionary definitions, definitions in documents incorporated by reference, and/or ordinary meanings of the defined terms.

The present disclosure provides systems and methods for producing aromatic hydrocarbons at high yield and purity. Exemplary aromatic hydrocarbons include, but are not limited to, benzene, toluene, ethyl benzene, para-xylene, meta-xylene, ortho-xylene, dimethyl benzene, and naphthalene. The provided systems and methods may produce aromatics with high purity, e.g., at least 98.5%, or at least 99%, or at least 99.5%, or at least 99.9%.

The provided systems and methods offer various advantages. For example, processing of mixed aromatic feed streams typically requires separation steps, such as extraction, to produce high purity aromatics. In some embodiments, the provided systems and methods obtain high purity aromatics without implementing extraction techniques to remove impurities from the feed stream. Removing extraction from the separation scheme reduces energy requirements, as well as capital costs. Some aromatic products are more difficult to separate compared to others. For example, in some embodiments of the present disclosure, xylene isomers (e.g., para-xylene) can be purified using an isomer-recovery process unit (e.g., adsorption or crystallization) coupled with an isomerization stage and distillation. Crystallization and adsorption processes require a considerable amount of energy in the form of heat and electricity to separate out xylene isomers from intermediate products. In one aspect of the present disclosure, systems and methods are provided for reducing the energy burden of the separations by allowing a portion of an intermediate stream to pass directly into an isomer-recovery process unit without distillation, or bypassing a portion of the distillation units, thereby eliminating the energy associated with the bypassed distillation. This reduces the overall system energy burden, and surprisingly maintains acceptable product purity despite bypassing purification stages.

In another aspect of the present disclosure, systems and methods are provided for producing a mixed aromatic feed stream that is free of or substantially free of co-boiling nonaromatic contaminants for benzene, toluene, and a combination thereof. As used herein, the term "substantially free" refers to less than 1% (w/w) of the specified compound or mixture of compounds in the specified stream. In some embodiments, the mixed aromatic feed stream comprises less than 1% (w/w), or less than 0.5% (w/w), or less than 0.1% (w/w) co-boiling nonaromatic contaminants for benzene, toluene, and a combination thereof. By feeding the mixed aromatic feed stream over a transalkylation and/or a dealkylation catalyst where co-boiling nonaromatic contaminants are absent, or substantially absent, aromatic products having higher purity and yield are obtained when compared to a mixed aromatic stream comprising nonaromatic contaminants.

As used herein, the term "co-boiling non-aromatic contaminant" refers to non-aromatic species that cannot be separated from, or only separated from with great difficulty, the desired products by distillation. The co-boiling non-aromatics are different for each desired product and may include hydrocarbons, oxygenates, sulfur containing species, and nitrogen containing species. The benzene co-boiling range is defined here as all components (including benzene) with normal boiling points equal to or greater than methylcyclopentane (normal boiling point 71.8° C.) and less than or equal to that of 1, 3 dimethylcyclopentane, cis (normal boiling point 91° C.). Exemplary co-boiling non-aromatic contaminants for benzene include, but are not limited to, methylcyclopentane, cyclohexane, methylcyclopentenes, $C_7$ paraffins, and $C_7$ olefins.

The co-boiling range for toluene is defined here as all components (including toluene) with retention times greater than, and including 1,3 dimethylcyclopentane, cis (boiling point 91° C.) and less than, and including trans 1,2-dimethyl-cyclohexane (boiling point 123° C.).

Referring to FIG. 1, an aromatics purification system 10 is illustrated in accordance to some aspects of the present disclosure. For clarity and simplicity, equipment for controlling temperature and flows within aromatics purification system 10 have been omitted from the drawings. However, it is to be appreciated that the aromatics purification system 10 can include various equipment for controlling temperature (e.g., heat exchangers, fired heater, coolers, electrical heaters, or combinations thereof for heating or cooling process streams), even though it has been omitted from the drawings. The aromatics purification system 10 can include equipment for controlling flow rate of fluid including, but not limited to, pumps, valves, compressors, blowers, or combinations thereof for regulating the flow of fluid throughout the system 10, even though it has been omitted from the drawings.

In some aspects, the aromatics purification system 10 includes an aromatics processing reactor 12 having an inlet that places the aromatics processing reactor 12 in fluid communication with a mixed aromatic feed stream 14. A pump may be configured in the mixed aromatic feed stream 14 to transport the mixed aromatic feed stream 14 from a mixed aromatic feed source 16, such as a reservoir or upstream process unit, to the aromatics processing reactor 12. In some embodiments, the mixed aromatic feed stream 14 is optionally combined with a $C_7$ stream 36 and a $C_{9-10}$ stream 46, which are further defined below.

In some embodiments, the mixed aromatic feed stream 14 or combined mixed aromatic feed stream 15 comprises non-aromatic compounds and aromatic compounds, which may be derived from a variety of original sources including, without limitation, biomass derived oxygenates and condensation products, petroleum refining, thermal or catalytic cracking of hydrocarbons, coking of coal, petrochemical conversions, or combinations thereof.

In some embodiments, the mixed aromatic feed stream 14 or combined mixed aromatic feed stream 15 comprises from 0.1 wt % to 45 wt % non-aromatic hydrocarbons, e.g., paraffins, olefins, naphthenes, naphtheno-olefins, or combinations thereof. In some embodiments, the hydrocarbon feed stream comprises at least 0.1 wt % non-aromatic hydrocarbons, or at least 1 wt %, or at least 2 wt % or at least 3 wt %, or at least 4 wt %, or at least 5 wt %, or at least 10 wt %, or at least 15 wt %, or at least 20 wt %, to less than 25 wt %, less than 30 wt %, or less than 35 wt %, or less than 40 wt %, or less than 45 wt %. In some embodiments, the hydrocarbon feed stream comprises $C_{3-30}$ paraffins, $C_{3-30}$ olefins, $C_{5-30}$ naphthenes, or combinations thereof.

As used herein, the term "paraffin" or "alkane" refers to a $C_{3-30}$ saturated straight-chain or branch-chain hydrocarbons. In some embodiments, the paraffins have a general formula of $C_nH_{2n+2}$, where n may range from 3 to 30, from 3 to 25, from 3 to 20, from 3 to 15, from 3 to 10, or from 3 to 6.

As used herein, the term "olefin" or "alkene" refers to a $C_{3-30}$ unsaturated straight-chain or branch-chain hydrocarbon having at least one carbon-carbon double bond. In some embodiments, the olefins have a general formula of $C_nH_{2n}$, where n may range from 3 to 30, from 3 to 25, from 3 to 20, from 3 to 15, from 3 to 10, or from 3 to 6.

Examples of various paraffins and olefins include, without limitation, propane, propene, butane, butene, pentane, pentene, 2-methylbutane, hexane, hexene, 2-methylpentane, 3-methylpentane, 2,2-dimethylbutane, 2,3-dimethylbutane, heptane, heptene, octane, octene, 2,2,4,-trimethylpentane, 2,3-dimethyl hexane, 2,3,4-trimethylpentane, 2,3-dimethylpentane, nonane, nonene, decane, decene, undecane, undecene, dodecane, dodecene, tridecane, tridecene, tetradecane, tetradecene, pentadecane, pentadecene, hexadecane, hexadecene, heptyldecane, heptyldecene, octyldecane, octyldecene, nonyldecane, nonyldecene, eicosane, eicosene, uneicosane, uneicosene, doeicosane, doeicosene, trieicosane, trieicosene, tetraeicosane, tetraeicosene, and isomers thereof.

In some embodiments, the mixed aromatic feed stream 14 or the combined mixed aromatic feed stream 15 comprises at least 0.1 wt % olefins, or at least 1 wt %, or at least 2 wt % or at least 3 wt %, or at least 4 wt %, or at least 5 wt %, or at least 10 wt %, or at least 15 wt %, or at least 20 wt %, to less than 25 wt %, less than 30 wt %, or less than 35 wt %, or less than 40 wt %, or less than 45 wt % olefins.

As used herein, the term "naphthene" or "cycloalkane" refers to a saturated cyclic, bicyclic, or bridged cyclic hydrocarbon group. The saturated cyclic, bicyclic, or bridged cyclic (e.g., adamantane) hydrocarbon group may be substituted with one or more straight-chain or branched-chain alkyl group or alkylene group, e.g., the substituted group(s) may include a straight-chain or branched-chain $C_1$-12 alkyl, a straight-chain or branched-chain $C_{3-12}$ alkylene, a straight-chain or branched-chain $C_{1-4}$ alkyl, a straight-chain or branched-chain $C_{3-4}$ alkylene. The naphthene may be mono-substituted or multi-substituted. In some embodiments, the naphthene have a general formula of $C_nH_{2n}$, where n may range from 5 to 30, from 5 to 25, from 5 to 20, from 5 to 15, from 5 to 10, or from 5 to 6.

Examples of naphthenes include, without limitation, cyclopentane, cyclopentene, cyclohexane, cyclohexene, methyl-cyclopentane, methyl-cyclopentene, ethyl-cyclopentane, ethyl-cyclopentene, ethyl-cyclohexane, ethyl-cyclohexene, propyl-cyclohexane, butyl-cyclopentane, butyl-cyclohexane, pentyl-cyclopentane, pentyl-cyclohexane, hexyl-cyclopentane, hexyl-cyclohexane, decalin, ethyl-decalin, pentyl-decalin, hexyl-decalin, and isomers thereof.

In some embodiments, the mixed aromatic feed stream 14 or the combined mixed aromatic feed stream 15 comprises at least 0.1 wt % naphthene, or at least 1 wt %, or at least 2 wt % or at least 3 wt %, or at least 4 wt %, or at least 5 wt %, or at least 6 wt %, or at least 7 wt %, or at least 8 wt %, or at least 9 wt %, or at least 10 wt %, to less than 11 wt %, or less than 12 wt %, or less than 13 wt %, or less than 14 wt %, or less than 15 wt % or less than 16 wt %, or less than 17 wt %, or less than 18 wt %, or less than 19 wt %, or less than 20 wt %, or less than 21 wt %, or less than 22 wt %, or less than 23 wt %, or less than 24 wt %, or less than 25 wt % naphthene.

As used herein, the term "naphtheno-olefin" refers to a saturated cyclic, bicyclic, or bridged cyclic hydrocarbon group having a mono-substituted olefin or a multi-substituted olefin on the hydrocarbon group. In some embodiments, the mixed aromatic feed stream 14 or the combined mixed aromatic feed stream 15 comprises at least 0.1 wt % naphtheno-olefins, or at least 1 wt %, or at least 2 wt % or at least 3 wt %, or at least 4 wt %, or at least 5 wt %, or at least 10 wt %, or at least 15 wt %, or at least 20 wt %, to less than 25 wt %, less than 30 wt %, or less than 35 wt %, or less than 40 wt % naphtheno-olefins.

In some embodiments, the mixed aromatic feed stream 14 or the combined mixed aromatic feed stream 15 comprises from 10 wt % to 80 wt % aromatic hydrocarbons, e.g., aryls, fused aryls, polycyclic compounds, or combinations thereof. In some embodiments, the hydrocarbon feed stream comprises at least 10 wt % aromatic hydrocarbons, or at least 10 wt %, or at least 15 wt % or at least 20 wt %, or at least 25 wt %, or at least 30 wt %, or at least 35 wt %, or at least 40 wt %, or at least 45 wt %, to less than 50 wt %, less than 55 wt %, or less than 60 wt %, or less than 65 wt %, or less than 75 wt %, or less than 80 wt % aromatics. In some embodiments, the hydrocarbon feed stream comprises a plurality of $C_{6-30}$ aryls, $C_{12-30}$ fused aryls, $C_{12-30}$ polycylic compounds, or combinations thereof.

As used herein, the term "aryls" and "aromatics" refers to an aromatic hydrocarbon in an unsubstituted (phenyl), mono-substituted, or multi-substituted form. In the case of mono-substituted and multi-substituted compounds, the substituted group may include a branched $C_{3+}$ alkyl, a straight-chain $C_{1+}$ alkyl, a branched-chain $C_{3+}$ alkylene, a straight chain $C_{2+}$ alkylene, or a combination thereof. By way of example, at least one of the substituted groups include a branched-chain $C_{3+}$ alkyl, a straight-chain $C_{1-12}$ alkyl, a branched-chain $C_{3-12}$ alkylene, a straight-chain $C_{2-12}$ alkylene, or a combination thereof. By way of further example, at least one of the substituted groups include a branched $C_{3-4}$ alkyl, a straight chain $C_{1-4}$ alkyl, a branched $C_{3-4}$ alkylene, straight chain $C_{2-4}$ alkylene, or a combination thereof. Examples of various aryls include, without limitation, benzene, toluene, xylene (dimethylbenzene), ethyl benzene, para-xylene, meta-xylene, ortho-xylene, $C_{9+}$ aromatics, butyl benzene, pentyl benzene, hexyl benzene, heptyl benzene, octyl benzene, nonyl benzene, decyl benzene, undecyl benzene, and isomers thereof.

In some embodiments, the mixed aromatic feed stream 14 or the combined mixed aromatic feed stream 15 comprises phenols in an amount of at least 10 ppm to less than 10 wt %, based on the total weight of the feed stream. In some embodiments, the mixed aromatic feed stream 14 or the combined mixed aromatic feed stream 15 comprises at least 10 ppm phenols, or at least 50 ppm, or at least 100 ppm, or at least 200 ppm, or at least 300 ppm, or at least 400 ppm, or at least 500 ppm, or at least 600 ppm, or at least 700 ppm or at least 800 ppm, or at least 900 ppm, or at least 0.1 wt %, or at least 1 wt %, or at least 2 wt %, or at least 3 wt %, or at least 4 wt %, to less than 5 wt %, or less than 6 wt %, or less than 7 wt %, or less than 8 wt %, or less than 9 wt %, or less than 10 wt % phenols, based on the total weight of the feed stream.

As used herein, the term "fused aryl" or "polynuclear aromatic (PNA)" refers to bicyclic and polycyclic aromatic hydrocarbons, in either an unsubstituted, mono-substituted, or multi-substituted form. In the case of mono-substituted and multi-substituted compounds, the substituted group may include a branched-chain $C_{3-12}$ alkyl, a straight-chain $C_{1-12}$ alkyl, a branched-chain $C_{3-12}$ alkylene, a straight-chain $C_{2-12}$ alkylene, a branched-chain $C_{3-4}$ alkyl, a straight-chain $C_{1-4}$ alkyl, a branched-chain $C_{3-4}$ alkylene, straight-chain $C_{2-4}$ alkylene, or a combination thereof. Examples of various fused aryls include, without limitation, naphthalene, anthracene, and isomers thereof.

As used herein, the term "polycyclic compounds" refers to bicyclic and polycyclic hydrocarbons having at least one saturated or partially saturated ring, in either an unsubstituted, mono-substituted, or multi-substituted form. In the case of mono-substituted and multi-substituted compounds, the substituted group may include a branched-chain $C_{3-12}$ alkyl, a straight-chain $C_{1-12}$ alkyl, a branched-chain $C_{3-12}$ alkylene, a straight-chain $C_{2-12}$ alkylene, a branched-chain $C_{3-4}$ alkyl, a straight-chain $C_{1-4}$ alkyl, a branched-chain $C_{3-4}$ alkylene, straight-chain $C_{2-4}$ alkylene, or a combination thereof. Examples of various polycyclic compounds include, without limitation, tetralin (i.e., tetrahydronaphthalene), ethyl-tetralin, pentyl-tetralin, hexyl-tetralin, and isomers thereof.

In some embodiments, the mixed aromatic feed stream 14 or combined mixed aromatic feed stream 15 has a bromine number of at least 1 mg $Br_2$/g feed to less than 100 $Br_2$/g feed. In some embodiments, the mixed aromatic feed stream 14 or combined mixed aromatic feed stream 15 has a bromine number greater than 1 mg $Br_2$/g, or at least 5 mg $Br_2$/g, or at least 10 mg $Br_2$/g, or at least 15 mg $Br_2$/g, or at least 20 mg $Br_2$/g, or at least 25 mg $Br_2$/g, or at least 30 mg $Br_2$/g, or at least 40 mg $Br_2$/g, or at least 50 mg $Br_2$/g, or less than 60 mg $Br_2$/g, or less than 70 mg $Br_2$/g, or less than 80 mg $Br_2$/g, or less than 90 mg $Br_2$/g, or less than 100 mg $Br_2$/g. The bromine number is a measure of aliphatic unsaturation in the feed. The bromine number may be determined using known methods, such as ASTM D1159.

In some embodiments, the mixed aromatic feed stream 14 or combined mixed aromatic feed stream 15 comprises oxygenates in an amount from 10 ppm to less than 10 wt %, based on the total weight of the feed stream. In some embodiments, the mixed aromatic feed stream 14 or the combined mixed aromatic feed stream 15 comprises at least 10 ppm oxygenates, or at least 50 ppm, or at least 100 ppm, or at least 200 ppm, or at least 300 ppm, or at least 400 ppm, or at least 500 ppm, or at least 600 ppm, or at least 700 ppm or at least 800 ppm, or at least 900 ppm, or at least 0.1 wt %, or at least 1 wt %, or at least 2 wt %, or at least 3 wt %, or at least 4 wt %, to less than 5 wt %, or less than 6 wt %, or less than 7 wt %, or less than 8 wt %, or less than 9 wt %, or less than 10 wt % oxygenates, based on the total weight of the feed stream.

As used herein, the term "$C_{n+}$," refers to a hydrocarbon compound having n carbons or greater in the compound (e.g., at least 7 carbons), and the term "$C_{n-}$" refers to a hydrocarbon compound having n carbons or fewer in the compound (e.g., less than 7 carbon atoms). In some embodiments, the mixed aromatic feed stream 14 or the combined mixed aromatic feed stream 15 comprises $C_{7+}$ aromatic hydrocarbons. In some embodiments, the mixed aromatic feed stream 14 or the combined mixed aromatic feed stream 15 is composed of $C_{7-10}$ aromatics, $C_{8-10}$ aromatics, or $C_{9-10}$ aromatics. In some embodiments, the mixed aromatic feed stream 14 or the combined mixed aromatic feed stream 15 is free of or substantially free of heavy aromatics, such as $C_{11+}$ compounds. In some embodiments, the mixed aromatic feed stream 14 or the combined mixed aromatic feed stream 15 is free of or substantially free of co-boiling contaminants for benzene, toluene, or a combination thereof.

Figure 2:
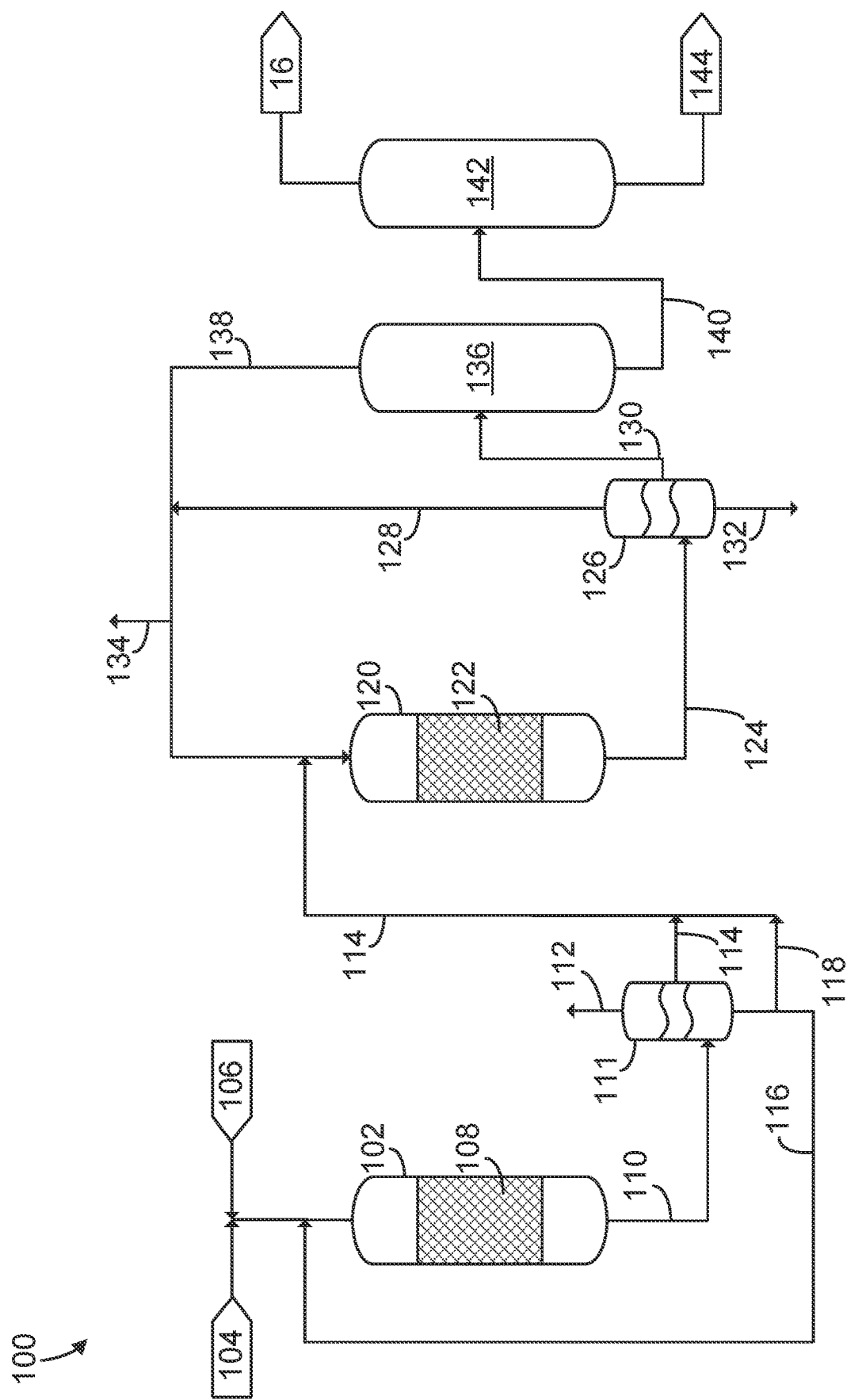
FIG. 2 is a schematic illustration of a process configured to convert oxygenated hydrocarbons to form a mixed aromatic feed stream in accordance with some embodiments of the present disclosure.

As will be described in greater detail with reference to FIG. 2, the mixed aromatic feed stream 14 may be produced from water-soluble sugars derived from biomass. Additionally or alternatively, the mixed aromatic feed stream 14 may be derived from a variety of original sources including, but not limited to, petroleum refining, thermal or catalytic cracking of hydrocarbons, coking of coal, or petrochemical conversions.

Referring back to FIG. 1, the aromatics processing reactor 12 may optionally include a hydrogen inlet that places the aromatics processing reactor 12 in fluid communication with a hydrogen stream 18. A gas transport device may be configured in the hydrogen stream 18 to transport hydrogen from a hydrogen source 20, such as a reservoir or upstream process unit, to the aromatics processing reactor 12.

The aromatics processing reactor 12 comprises an aromatic processing catalyst 22 that is configured to reform the mixed aromatic feed stream 14 to produce a product stream having an increased concentration of $C_8$ aromatics relative to the aromatic feed stream 14 or the combined aromatic feed stream 15. Suitable aromatic processing catalysts 22 include, but are not limited to, a transalkylation catalyst, a dealkylation catalyst, a hydrocracking catalyst, or combinations thereof. In some embodiments, the aromatic processing catalyst 22 may be composed of a bi-functional acidic, metal containing catalyst. The aromatic processing catalyst 22 may include, without limitation, carbides, nitrides, zirconia, alumina, silica, aluminosilicates, phosphates, zeolites (e.g., ZSM-5, ZSM-11, ZSM-12, ZSM-22, ZSM-23, ZSM-35 and ZSM-48), titanium oxides, zinc oxides, vanadium oxides, lanthanum oxides, yttrium oxides, scandium oxides, magnesium oxides, cerium oxides, barium oxides, calcium oxides, hydroxides, heteropolyacids, inorganic acids, acid modified resins, base modified resins, and combinations thereof.

In some embodiments, the aromatics processing catalyst 22 may include the above alone or in combination with a modifier, such as Ce, La, Y, Sc, P, B, Bi, Li, Na, K, Rb, Cs, Mg, Ca, Sr, Ba, or combinations thereof. The aromatics processing catalyst 22 may also include a metal, such as Cu, Ag, Au, Pt, Ni, Fe, Co, Ru, Zn, Cd, Ga, In, Rh, Pd, Ir, Re, Mn, Cr, Mo, W, Sn, Os, alloys or combinations thereof, to provide a metal functionality.

In some embodiments, the aromatics processing reactor 12 is operated as a gas phase reactor in which the optional hydrogen and the aromatic feed stream 14 are introduced into the aromatics processing reactor 12 and allowed to flow downward over a fixed bed of the aromatics processing catalyst 22. Alternatively, the aromatics processing reactor 12 operates as a radial flow or upflow reactor. In other embodiments, the reactor 12 is operated as a fixed, trickle bed reactor in which the optional hydrogen and combined aromatic feed stream are introduced into the reactor 12 and allowed to flow downward over a fixed bed of the catalyst 22. Although the hydrogen conduit 18 and the combined aromatic stream 14 are depicted in a co-current direction in FIG. 1, it is to be appreciated that a countercurrent orientation could be implemented.

In some embodiments, the aromatics processing reactor 12 operates at a temperature from 200° C. to 600° C., 250° C. to 550° C., or from 300° C. to 500° C. In some embodiments, the pressure of the aromatics processing reactor 12 ranges from atmospheric pressure to 1500 psig. In some embodiments, the reactor 12 operates at a weight hourly space velocity (WHSV) from 0.1 to 10 mass feed/ mass catalyst/hour, or from 0.5 to 8 WHSV.

The product stream 24 exits the aromatics processing reactor 12 through a reactor outlet that is cooled to condense the aromatics, and is transported to a separator 25 that removes unreacted hydrogen and non-condensable compounds from the product stream 24. Cooling of reactor outlet stream 24 may be accomplished using one or more heat exchangers. A portion of the unreacted hydrogen may be optionally recycled and combined with the hydrogen stream 18 via a gas outlet 29. Recycle of the unreacted hydrogen can be achieved through the use of a gas transport device, such as a compressor or blower. The liquid product stream 27 from the separator 25 is then subject to distillation to recover various product fractions. The order in which the fractions are recovered may differ depending on implementation specifics.

In one embodiment, the liquid product stream 27 from the separator 25 is directed to a first distillation column 26. A pump may be configured in the liquid product stream 27 to facilitate transport of the liquid product stream 27, and a heat exchanger may be configured in the liquid product stream 27 to control the temperature of the liquid product stream entering the first distillation column 26. A valve may be positioned in the product stream 27 to regulate the flow. The first distillation column 26 fractionates the liquid product stream 27 into a $C_{7-}$ stream 28 and a $C_{8+}$ stream 30. Although FIG. 1 depicts the first distillation column 26 as a single column, it is to be appreciated that fractionating the liquid product stream 27 into the $C_{7-}$ stream 28 and the $C_{8+}$ stream 30 could occur over multiple distillation columns.

In some embodiments, the $C_{7-}$ stream 28 is fed to a second distillation column 32 that fractionates the $C_{7-}$ stream 28 into a $C_{6-}$ stream 34 and a $C_7$ stream 36. In some embodiments, the $C_{6-}$ stream 34 is collected or discarded from the process. The $C_{6-}$ stream 34 may be optionally further processed in an aromatics purification unit to isolate a product from the $C_{6-}$ stream 34. For example, the $C_{6-}$ stream 34 may be subjected to further distillation, crystallization, or adsorption to isolate benzene from the $C_{6-}$ stream 34. In some embodiments, at least a portion of the $C_{6-}$ stream 34 is recycled to an upstream process unit, such as an acid condensation catalyst, to produce more $C_8$ aromatics or other desired aromatics.

In some embodiments, at least a portion of the $C_7$ stream 36 is recycled and combined with the mixed aromatic feed stream 14 to form the combined mixed aromatic feed stream 15 such that the $C_7$ stream 36 can be further reacted over the aromatics processing catalyst 22. Additionally or alternatively, at least a portion of the $C_7$ stream 36 may collected or discarded from the process. The collected or discarded portion of the $C_7$ stream 36 may be optionally further processed in an aromatics purification unit to isolate a product from the $C_7$ stream 36. For example, the $C_7$ stream 36 may be subjected to further distillation, crystallization, or adsorption to isolate toluene from the $C_7$ stream 36.

In some embodiments, the $C_{8+}$ stream 30 exiting the first distillation column 26 is fed to a third distillation column 38. The third distillation column 38 fractionates the $C_{8+}$ stream 30 into a $C_8$ stream 40 and a $C_{9+}$ stream 42. In some embodiments, at least a portion of the $C_{8+}$ stream 30 optionally bypasses the third distillation column 38 such that the portion of the $C_{8+}$ stream 30 is combined with the $C_8$ stream 40 exiting the third distillation column 38. The bypass stream offers various advantages. First, bypassing the third distillation column 38 reduces the overall system energy burden by lowering the flux of material passing through the distillation column 38, thereby lowering operation costs. Further, Applicant has surprisingly and unexpectedly found that incorporating the bypass stream lowers operation costs while still maintaining acceptable product purity, despite bypassing the distillation column 38.

In some embodiments, the $C_{9+}$ stream 42 is fed to a fourth distillation column 44. The fourth distillation column fractionates the $C_{9+}$ stream 42 into a $C_{9-10}$ stream 46 and a $C_{11+}$ stream 48. In some embodiments, at least a portion of the $C_{9-10}$ stream 46 is recycled and combined with the mixed aromatic feed stream 14 to form the combined mixed aromatic feed stream 15 such that the $C_{9-10}$ stream 46 can be further reacted over the aromatics processing catalyst 22. Additionally or alternatively, at least a portion of the $C_{9-10}$ stream 46 may collected or discarded from the process. The collected or discarded portion of the $C_{9-10}$ stream 46 may be optionally further processed in an aromatics purification unit to isolate a product from the $C_{9-10}$ stream 46. For example, the $C_{9-10}$ stream 46 may be subjected to further distillation, crystallization, or adsorption to isolate naphthalene from the $C_{9-10}$ stream 46. In some embodiments, the $C_{11+}$ stream 48 is discarded from the system, or further processed in downstream process units. For example, the $C_{11+}$ stream be collected or further separated for diesel fuel use or as lubricants or fuel oils. Additionally or alternatively, the $C_{11+}$ stream may be cracked, separated, and recycled to either the mixed aromatic feed stream or an acid condensation catalyst for further processing.

In some embodiments, the $C_8$ stream 40 is fed to an isomer-recovery process unit 50. The isomer-recovery process unit 50 is configured to produce a xylene isomer stream 52 and a raffinate stream 54 comprising non-recovered $C_8$ compounds. Exemplary isomer-recovery process units 50 include, but are not limited to, crystallization units, adsorption units, or a combination thereof, that are configured to selectively purify a xylene isomer from the $C_8$ stream 40. The isomer-recovery process unit 50 may be configured to purify para-xylene, ortho-xylene, or meta-xylene from the $C_8$ stream 40.

In some embodiments, the raffinate stream 54 comprising non-recovered $C_8$ compounds is fed to an isomerization reactor 56. A pump and valve may be configured in the raffinate stream 54 to regulate the flow of raffinate to the isomerization reactor 56. The isomerization reactor 56 comprises an isomerization catalyst 58 that is configured to produce an isomerization product stream comprising an increased concentration of the desired xylene isomer (e.g., para-xylene, ortho-xylene, or meta-xylene) with minimal conversion to lighter and heavier products. The isomerization reactor 56 may optionally include a hydrogen inlet that places the isomerization reactor 56 in fluid communication with a hydrogen stream 59. A gas transport device may be configured in the hydrogen stream 59 to transport hydrogen from a hydrogen source 57, such as a reservoir or upstream process unit, to the isomerization reactor 56. In some embodiments, the hydrogen sources 20, 57 are derived from the same reservoir or upstream process unit.

In some embodiments, the isomerization catalyst 58 is composed of alumina, silica, aluminosilicates, zeolites (e.g., ZSM-5, ZSM-11, ZSM-12, ZSM-22, ZSM-23, ZSM-35 and ZSM-48), and combinations thereof. In some embodiments, the isomerization catalyst 58 includes the above alone or in combination with a modifier, such as Ce, La, Y, Sc, P, B, Bi, Li, Na, K, Rb, Cs, Mg, Ca, Sr, Ba, and combinations thereof. The isomerization catalyst 58 may also include a metal, such as Cu, Ag, Au, Pt, Ni, Fe, Co, Ru, Zn, Cd, Ga, In, Rh, Pd, Ir, Re, Mn, Cr, Mo, W, Sn, Os, alloys and combinations thereof, to provide a metal functionality. The isomerization reactor 56 may be operated as a fixed, trickle bed reactor or as a slurry reactor. In some embodiments, the isomerization reactor 56 is operated at a temperature from 100° C. to 500° C., at a pressure from atmospheric pressure to 1500 psig, and at a WHSV from 0.1 to 10 mass feed/mass catalyst/hour.

In some embodiments, at least a portion of the isomerization product stream 60 exits through a reactor outlet that is cooled to condense the products, and is transported to a separator 61 that removes unreacted hydrogen and non-condensable compounds from the isomerization product stream 60. Cooling of the isomerization product stream 60 may be accomplished using one or more heat exchangers. A portion or all of the unreacted hydrogen may be optionally recycled and combined with the hydrogen stream 59 via a gas outlet 63. Recycle of the unreacted hydrogen can be achieved through the use of a gas transport device, such as a compressor or blower. The liquid product stream 65 from the separator 61 is the transported to the first distillation column 26 for fractionation. In some embodiments, the liquid product stream 65 from the separator 61 is optionally recycled and combined with the liquid product stream 27 from the separator 25 prior to being transported to the first distillation column 26.

In some embodiments, at least a portion of the isomerization product 60 is optionally recycled and combined with the $C_8$ stream 40 exiting the third distillation column 38. For example, a portion of the liquid product stream 65 may be split into stream 62, which is then transported and combined with the $C_8$ stream 40. The bypass stream 62 offers various advantages. As discussed above, bypassing the distillation columns 26, 32, 38 reduces the overall system energy burden by lowering the flux of material passing through the distillation columns, thereby lowering operation costs. Further, Applicant has surprisingly and unexpectedly found that incorporating the bypass stream 62 lowers operation costs while still maintaining acceptable product purity, despite bypassing the distillation columns 26, 32, and 38. For example, a product purity of at least 98.5%, or at least 99%, or at least 99.5% can be obtained in the xylene stream 52 when operating with one or both of the bypass streams 30 and 60.

In some embodiments, the mixed aromatic feed stream 14 may be produced from biomass-derived oxygenated hydrocarbons. An exemplary system 100 for producing the mixed aromatic feed stream 14 from biomass-derived oxygenated hydrocarbons is depicted in FIG. 2. In some embodiments, the system 100 includes a hydrodeoxygenation (HDO) reactor 102 in fluid communication with a feedstock solution source 104 and a hydrogen source 106.

In some embodiments, the feedstock solution source 104 includes a feedstock solution including water-soluble sugars derived from biomass. As used herein, the term "biomass" refers to, without limitation, organic materials produced by plants (such as leaves, roots, seeds and stalks), and microbial and animal metabolic wastes. Common biomass sources include: (1) agricultural wastes, such as corn stalks, straw, seed hulls, sugarcane leavings, bagasse, nutshells, and manure from cattle, poultry, and hogs; (2) wood materials, such as wood or bark, sawdust, timber slash, and mill scrap; (3) municipal waste, such as waste paper and yard clippings; and (4) energy crops, such as poplars, willows, switch grass, alfalfa, prairie bluestream, corn, soybean, and the like.

Various sugar processing methods are well known in the art and commercially practiced at large scale for producing a sugar solution from biomass. For example, in processes using sugar cane, the sugar cane is generally washed, crushed or diffused, and lime clarified to isolate and provide an aqueous biomass-derived intermediate feedstock stream rich in sucrose, fructose, and glucose. In processes using sugar beets, the sugar beets are likewise washed, sliced, extracted, and clarified to isolate and provide an aqueous biomass-derived intermediate feedstock stream in sucrose, fructose, and glucose. For processes involving cereal grains, the cereal grain is cleaned and then processed to provide wet milled starches (corn) or dry milled/ground starches (corn, wheat, barley, sorghum grain). The isolated sugar solution may be adjusted to obtain a desired sugar concentration, e.g., can be concentrated or diluted with water to provide the feedstock solution 104. Generally, a suitable concentration is in the range of about 5% to about 70%, with a range of about 40% to 70% more common in industrial applications.

For a raw feedstock of lignocellulosic biomass, the biomass feed may be deconstructed from complex biopolymers into sugars and soluble oxygenates to form the feedstock solution 104.

In one embodiment, the raw lignocellulosic feedstock (such as corn stover) undergoes deconstruction by dilute acid thermochemical pretreatment, pH adjustment by base such as ammonium hydroxide, lime, sodium hydroxide or potassium hydroxide and enzymatic hydrolysis to form soluble sugars. Optional preconversion methods include fractionation in the harvesting of the feedstock, fractionation by sieving, chemical preprocessing to leach out undesired components, fermentative preprocessing such as treatment by white rot fungi, mechanical methods such as steam explosion, torrefaction, or pelleting. Alternate means of deconstruction include thermochemical pretreatment by autohydrolysis (hot water only), alkali (for example, ammonia, sodium hydroxide, potassium hydroxide), oxidation (for example, peroxide, oxygen, air), organosolv (for example, ethanol, acetic acid, catalytically-derived solvents), and ionic liquids. The processing step of lignocellulosic biomass may also include additional processing to provide biomass that has been chopped, shredded, pressed, ground or processed to a size amenable for conversion.

In some embodiments, the feedstock solution 104 may be formed using one or more of the aforementioned processes, and may be derived from one or more of the aforementioned biomass sources. The feedstock solution can be fabricated from biomass by any means now known or developed in the future, or can be simply byproducts of other processes.

In some embodiments, the feedstock solution comprises one or more oxygenated hydrocarbon. The term "oxygenated hydrocarbon" refers to a water-soluble hydrocarbon containing three or more carbon atoms and two or more oxygen atoms, such as carbohydrates (e.g., monosaccharides, disaccharides, oligosaccharides, polysaccharides, and starches), sugars (e.g., glucose, sucrose, xylose, etc.), sugar alcohols (e.g., diols, triols, and polyols), and sugar degradation products (e.g., hydroxymethyl furfural (HMF), levulinic acid, formic acid, and furfural), each of which is represented herein as $C_{3+}$ $O_{2+}$. As used herein, the term "oxygenated compound" or "oxygenate" refers to a molecule having two or more carbon atoms and one or more oxygen atoms (i.e., $C_{2+}$ $O_{1+}$); the term "monooxygenates" refers to a hydrocarbon molecule containing two or more carbon atoms and one oxygen atom (i.e., $C_{2+}$ $O_1$); the term "dioxygenates" refers to a hydrocarbon molecule containing two or more carbon atoms and two oxygen atoms (i.e., $C_{2+}$ $O_2$); and the term "polyoxygenates" refers to a hydrocarbon molecule containing two or more carbon atoms and three or more oxygen atoms (i.e., $C_{2+}$ $O_{3+}$).

In addition to the oxygenated hydrocarbons, the feedstock may also include lignin, one or more extractives, one or more ash components, or one or more organic species (e.g., lignin derivatives). Extractives include terpenoids, stilbenes, flavonoids, phenolics, aliphatics, lignans, alkanes, proteinaceous materials, amino acids, and other inorganic products. Ash components include Al, Ba, Ca, Fe, K, Mg, Mn, P, S, Si, Zn, etc. Other organic species include 4-ethyl phenol, 4-ethyl-2-methoxy phenol, 2-methoxy-4-propyl phenol, vanillin, 4-propyl syringol, vitamin E, steroids, long chain hydrocarbons, long chain fatty acids, stilbenoids, etc.

In some embodiments, the feedstock solution 104 is optionally hydrogenated prior to conversion in the hydrodeoxygenation reactor 102. For example, the feedstock solution may be contacted with a hydrogenation catalyst in a reactor (now shown) at a hydrogenation temperature and a hydrogenation pressure to produce a hydrogenation product stream. Various processes are known for hydrogenating carboxylic acids. The hydrogenation catalyst generally includes Fe, Ru, Co, Pt, Pd, Ni, Re, Cu, and alloys or combinations thereof, either alone or with promoters such as Ag, Au, Cr, Zn, Mn, Mg, Ca, Cr, Sn, Bi, Mo, W, B, P, and alloys or combinations thereof. The hydrogenation catalyst may also include any one of several supports, depending on the desired functionality of the catalyst. Such supports may include carbon, silica, alumina, zirconia, titania, vanadia, ceria, silica-aluminate, zeolite, kieselguhr, hydroxyapatite, zinc oxide, magnesium oxide, chromia, and mixtures thereof.

In general, the hydrogenation reaction is carried out at hydrogenation temperatures of between about 80° C. to 350° C., and hydrogenation pressures in the range of about 50 psig to 5000 psig. The hydrogen used in the reaction may include in situ hydrogen generated from other reactions occurring in series or parallel within the reactor, external Hz, recycled Hz, or a combination thereof.

In some embodiments, the feedstock solution 104 includes carboxylic acids that may be hydrogenated. The extent to which the carboxylic acid feedstock stream is hydrogenated can be measured by the amount of molecular hydrogen consumed during hydrogenation and may range from 0.05 to 2.0 moles of molecular hydrogen consumed per mole of carboxylic acid groups in the feed. In general, the reaction should be conducted under conditions where the residence time of the carboxylic acid feedstock over the catalyst is appropriate to generate the desired oxygenates. For example, the residence time may be established at a weight hourly space velocity (WHSV) of between 0.01 and 30, or between 0.05 and 10, or between 0.1 and 5.

Referring back to FIG. 2, the feedstock solution 104 is contacted with the deoxygenation catalyst 108 in the presence of hydrogen to produce a deoxygenation product stream 110 comprising a mixture of one or more oxygenate. The deoxygenation product stream 110 may comprise a $H:C_{eff}$ ratio greater than or equal to 0.5 and less than 2, or from 0.8 to 1.8, or from 1 to 1.6, or from 1.2 to 1.6. In some embodiments, the $H:C_{eff}$ ratio is at least 0.5, or at least 0.6, or at least 0.7, or at least 0.8, or at least 0.9, or at least 1, or at least 1.1, or at least 1.2, to less than 1.3, or less than 1.4, or less than 1.5, or less than 1.6, or less than 1.8, or less than 1.9, or less than 2.0.

As used herein, the term "$H:C_{eff}$ ratio" is based on the amount of carbon, oxygen and hydrogen in the feed, and is calculated as follows:

$$H:C_{eff} = \frac{H - 2O}{C},$$

where H represents the number of hydrogen atoms, O represents the number of oxygen atoms, and C represents the number of carbon atoms. Water and molecular hydrogen (diatomic hydrogen, $H_2$) are excluded from the calculation. The $H:C_{eff}$ ratio applies both to individual components and to mixtures of components, but is not valid for components which contain atoms other than carbon, hydrogen, and oxygen. For mixtures, the C, H, and O are summed over all components exclusive of water and molecular hydrogen. The term "hydrogen" refers to any hydrogen atom, while the term "molecular hydrogen" is limited to diatomic hydrogen, $H_2$. In some embodiments, the $H:C_{eff}$ ratio may be controlled or modulated by varying the hydrogenation and hydrodeoxygenation catalyst and operating conditions (e.g., temperature, pressure, WHSV, feed source selection and concentration).

In some embodiments, the deoxygenation product stream 110 includes $C_{1+}O_{1-3}$ hydrocarbons, which are compounds having 1 or more carbon atoms and between 1 and 3 oxygen atoms, such as alcohols, ketones, aldehydes, furans, hydroxy carboxylic acids, carboxylic acids, diols and triols. In some embodiments, the $C_{1+}O_{1-3}$ hydrocarbons have from 1 to 6 carbon atoms, or 2 to 6 carbon atoms, or 3 to 6 carbon atoms. In addition to $C_{1+}O_{1-3}$ hydrocarbons, the deoxygenation product stream 110 may include hydrocarbons having no oxygen elements.

Exemplary alcohols in the deoxygenation product stream 110 may include, without limitation, primary, secondary, linear, branched or cyclic $C_{1+}$ alcohols, such as methanol, ethanol, n-propyl alcohol, isopropyl alcohol, butyl alcohol, isobutyl alcohol, butanol, pentanol, cyclopentanol, hexanol, cyclohexanol, 2-methyl-cyclopentanonol, heptanol, octanol, nonanol, decanol, undecanol, dodecanol, and isomers thereof. Exemplary ketones may include, without limitation, hydroxyketones, cyclic ketones, diketones, acetone, propanone, 2-oxopropanal, butanone, butane-2,3-dione, 3-hydroxybutan-2-one, pentanone, cyclopentanone, pentane-2,3-dione, pentane-2,4-dione, hexanone, cyclohexanone, 2-methyl-cyclopentanone, heptanone, octanone, nonanone, decanone, undecanone, dodecanone, methylglyoxal, butanedione, pentanedione, diketohexane, and isomers thereof. Exemplary aldehydes may include, without limitation, hydroxyaldehydes, acetaldehyde, propionaldehyde, butyraldehyde, pentanal, hexanal, heptanal, octanal, nonal, decanal, undecanal, dodecanal, and isomers thereof. Exemplary carboxylic acids may include, without limitation, formic acid, acetic acid, propionic acid, butanoic acid, pentanoic acid, hexanoic acid, heptanoic acid, isomers and derivatives thereof, including hydroxylated derivatives, such as 2-hydroxybutanoic acid and lactic acid. Exemplary diols may include, without limitation, ethylene glycol, propylene glycol, 1,3-propanediol, butanediol, pentanediol, hexanediol, heptanediol, octanediol, nonanediol, decanediol, undecanediol, dodecanediol, and isomers thereof. Exemplary triols may include, without limitation, glycerol, 1,1,1 tris(hydroxymethyl)-ethane (trimethylolethane), trimethylolpropane, hexanetriol, and isomers thereof. Exemplary furans and furfurals include, without limitation, furan, tetrahydrofuran, dihydrofuran, 2-furan methanol, 2-methyl-tetrahydrofuran, 2,5-dimethyl-tetrahydrofuran, 2-methyl furan, 2-ethyl-tetrahydrofuran, 2-ethyl furan, hydroxylmethylfurfural, 3-hydroxytetrahydrofuran, tetrahydro-3-furanol, 2,5-dimethylfuran, 5-hydroxymethyl-2(5H)-furanone, dihydro-5-(hydroxymethyl)-2(3H)-furanone, tetrahydro-2-furoic acid, dihydro-5-(hydroxymethyl)-2(3H)-furanone, tetrahydrofurfuryl alcohol, 1-(2-furyl)ethanol, hydroxymethyltetrahydrofurfural, and isomers thereof.

In some embodiments, the deoxygenation catalyst 108 is composed of a heterogeneous catalyst having one or more materials capable of catalyzing a reaction between hydrogen and a feedstock solution 104 to remove one or more of the oxygen atoms from the feedstock solution to produce one or more oxygenate. In some embodiments, the deoxygenation catalyst 108 is composed of one or more metal adhered to a support and may include, without limitation, Cu, Re, Fe, Ru, Ir, Co, Rh, Pt, Pd, Ni, W, Os, Mo, Ag, Au, alloys and combinations thereof. The deoxygenation catalyst may include these elements alone or in combination with one or more of Mn, Cr, Mo, W, V, Nb, Ta, Ti, Zr, Y, La, Sc, Zn, Cd, Ag, Au, Sn, Ge, P, Al, Ga, In, Tl, and combinations thereof. In one embodiment, the deoxygenation catalyst includes Pt, Ru, Cu, Re, Co, Fe, Ni, W or Mo. In yet another embodiment, the deoxygenation catalyst includes Fe or Re and at least one transition metal selected from Ir, Ni, Pd, P, Rh, or Ru. In another embodiment, the catalyst includes Fe, Re and at least Cu or one Group VIIIB transition metal. The support may be any one of the supports further described below, including a nitride, carbon, silica, alumina, zirconia, titania, vanadia, ceria, zinc oxide, chromia, boron nitride, heteropolyacids, kieselguhr, hydroxyapatite, and mixtures thereof.

The deoxygenation temperature may range from 80° C. to 300° C. In some embodiments, the reaction temperature is between about 120° C. and 600° C., or between about 200° C. and 280° C., or between about 220° C. and 260° C. The deoxygenation pressure may range from 72 psig to 1300 psig. In some embodiments, the deoxygenation pressure ranges from 72 to 1200 psig, or from 145 to 1200 psig, or from 200 to 725 psig, or from 365 to 700 psig, or between from 600 to 650 psig.

In some embodiments, the WHSV for the deoxygenation reaction ranges from 0.1 gram of oxygenated hydrocarbon per gram of catalyst per hour (g/g-hr) to 40 g/g-hr. In some embodiments, the WHSV is at least 0.25, at least 0.5, at least 0.75, at least 1.0, at least 1.1, at least 1.2, at least 1.3, at least 1.4, at least 1.5, at least 1.6, at least 1.7, at least 1.8, at least 1.9, at least 2.0, at least 2.1, at least 2.2, at least 2.3, at least 2.4, at least 2.5, at least 2.6, at least 2.7, at least 2.8, at least 2.9, at least 3.0, at least 3.1, at least 3.2, at least 3.3, at least 3.4, at least 3.5, at least 3.6, at least 3.7, at least 3.8, at least 3.9, at least 4.0, at least 4.1, at least 4.2, at least 4.3, at least 4.4, at least 4.5, at least 4.6, at least 4.7, at least 4.8, at least 4.9, at least 5.0, to less than 6, less than 7, less than 8, less than 9, less than 10, less than 11, less than 12, less than 13, less than 14, less than 15, less than 20, less than 25, less than 30, less than 35, or less than 40 g/g hr.

In some embodiments, the amount of hydrogen fed to the deoxygenation reactor 102 ranges from 0-2400%, 5-2400%, 10-2400%, 15-2400%, 20-2400%, 25-2400%, 30-2400%, 35-2400%, 40-2400%, 45-2400%, 50-2400%, 55-2400%, 60-2400%, 65-2400%, 70-2400%, 75-2400%, 80-2400%, 85-2400%, 90-2400%, 95-2400%, 98-2400%, 100-2400%, 200-2400%, 300-2400%, 400-2400%, 500-2400%, 600-2400%, 700-2400%, 800-2400%, 900-2400%, 1000-2400%, 1100-2400%, or 1150-2400%, or 1200-2400%, or 1300-2400%, or 1400-2400%, or 1500-2400%, or 1600-2400%, or 1700-2400%, or 1800-2400%, or 1900-2400%, or 2000-2400%, or 2100-2400%, or 2200-2400%, or 2300-2400%, based on the total number of moles of the oxygenated hydrocarbon(s) in the feedstock, including all intervals between. The hydrogen may be external hydrogen or recycled hydrogen. The term "external $H_2$" refers to hydrogen that does not originate from the feedstock solution, but is added to the reactor system from an external source. The term "recycled $H_2$" refers to unconsumed hydrogen, which is collected and then recycled back into the reactor system for further use.

In some embodiments, the product stream 110 is passed through a three-phase separator 111 to separate the product stream 110 into a non-condensed gas stream 112, an organic products stream 114, and an aqueous products stream 116. The non-condensed gas stream 112 may be composed of hydrogen, carbon dioxide, methane, ethane and propane. The non-condensed gasses may be removed and either combusted to create process heat (i.e., heat for driving the reaction in the deoxygenation reactor), or sent to a separation system where hydrogen can be recovered for recycling back to the hydrogen stream 106. The aqueous products stream 116, containing partially deoxygenated hydrocarbons, may be recycled back to the inlet of the deoxygenation reactor 102. An aqueous purge stream 118, including some monooxygenates (e.g., alcohols), can be used to prevent a build-up of water in the reactor system. The aqueous purge stream 118 can be combined with the organic products stream 114 or discarded from the process.

In some embodiments, the organic products stream 114 comprising oxygenates is passed through a condensation reactor 120 comprising a condensation catalyst 122. The oxygenates are converted into a condensation product stream 124 comprising $C_{4+}$ compounds by condensation reactions catalyzed by the condensation catalyst 122. Without being limited to any specific theories, it is believed that the condensation reactions generally consist of a series of steps involving: (a) the dehydration of oxygenates to alkenes; (b) oligomerization of the alkenes; (c) cracking reactions; (d) cyclization of larger alkenes to form aromatics; (e) alkane isomerization; (f) hydrogen-transfer reactions to form alkanes. The reactions may also consist of a series of steps involving: (1) aldol condensation to form a β-hydroxyketone or β-hydroxyaldehyde; (2) dehydration of the β-hydroxyketone or β-hydroxyaldehyde to form a conjugated enone; (3) hydrogenation of the conjugated enone to form a ketone or aldehyde, which may participate in further condensation reactions or conversion to an alcohol or hydrocarbon; and (4) hydrogenation of carbonyls to alcohols, or vice-versa. Other condensation reactions may occur in parallel, including aldol condensation, prins reactions, ketonization of acids, and Diels-Alder condensation.

The condensation catalyst 122 will generally be a catalyst capable of forming longer chain compounds by linking two oxygen containing species, or other functionalized compounds (e.g., olefins), through a new carbon-carbon bond, and converting the resulting compound to a hydrocarbon, alcohol or ketone. The condensation catalyst may include, without limitation, carbides, nitrides, zirconia, alumina, silica, aluminosilicates, phosphates, zeolites, titanium oxides, zinc oxides, vanadium oxides, lanthanum oxides, yttrium oxides, scandium oxides, magnesium oxides, cerium oxides, barium oxides, calcium oxides, hydroxides, heteropolyacids, inorganic acids, acid modified resins, base modified resins, and combinations thereof. The condensation catalyst may include the above alone or in combination with a modifier, such as Ce, La, Y, Sc, P, B, Bi, Li, Na, K, Rb, Cs, Mg, Ca, Sr, Ba, and combinations thereof. The condensation catalyst may also include a metal, such as Cu, Ag, Au, Pt, Ni, Fe, Co, Ru, Zn, Cd, Ga, In, Rh, Pd, Ir, Re, Mn, Cr, Mo, W, Sn, Os, alloys and combinations thereof, to provide a metal functionality.

In certain embodiments the condensation catalyst may include, without limitation, carbides, nitrides, zirconia, alumina, silica, aluminosilicates, phosphates, zeolites (e.g., ZSM-5, ZSM-11, ZSM-12, ZSM-22, ZSM-23, ZSM-35 and ZSM-48), titanium oxides, zinc oxides, vanadium oxides, lanthanum oxides, yttrium oxides, scandium oxides, magnesium oxides, cerium oxides, barium oxides, calcium oxides, hydroxides, heteropolyacids, inorganic acids, acid modified resins, base modified resins, and combinations thereof. The condensation catalyst may also include a metal, such as Cu, Ag, Au, Pt, Ni, Fe, Co, Ru, Zn, Cd, Ga, In, Rh, Pd, Ir, Re, Mn, Cr, Mo, W, Sn, Os, alloys and combinations thereof, to provide a metal functionality.

The condensation catalyst 122 may be self-supporting (i.e., the catalyst does not need another material to serve as a support), or may require a separate support suitable for suspending the catalyst in the reactant stream. In certain embodiments the support is selected from alumina, silica, or zirconia. In other embodiments, particularly when the condensation catalyst is a powder, the catalyst system may include a binder to assist in forming the catalyst into a desirable catalyst shape. Applicable forming processes include extrusion, pelletization, oil dropping, or other known processes. Zinc oxide, alumina, and a peptizing agent may also be mixed together and extruded to produce a formed material. After drying, this material is calcined at a temperature appropriate for formation of the catalytically active phase, which usually requires temperatures in excess of 350° C. Other catalyst supports may include those described in further detail below.

The condensation catalyst may include one or more zeolite structures comprising cage-like structures of silica-alumina. Zeolites are crystalline microporous materials with well-defined pore structures. Zeolites contain active sites, usually acid sites, which can be generated in the zeolite framework. The strength and concentration of the active sites can be tailored for particular applications. Examples of suitable zeolites for condensing secondary alcohols and alkanes may comprise aluminosilicates, optionally modified with cations, such as Ga, In, Zn, Mo, and mixtures of such cations, as described, for example, in U.S. Pat. No. 3,702,886, which is incorporated herein by reference. As recognized in the art, the structure of the particular zeolite or zeolites may be altered to provide different amounts of various hydrocarbon species in the product mixture. Depending on the structure of the zeolite catalyst, the product mixture may contain various amounts of aromatic and cyclic hydrocarbons.

Examples of suitable zeolite catalysts include ZSM-5, ZSM-11, ZSM-12, ZSM-22, ZSM-23, ZSM-35 and ZSM-48. Zeolite ZSM-5, and the conventional preparation thereof, is described in U.S. Pat. No. 3,702,886; Re. 29,948 (highly siliceous ZSM-5); U.S. Pat. Nos. 4,100,262 and 4,139,600, all incorporated herein by reference. Zeolite ZSM-11, and the conventional preparation thereof, is described in U.S. Pat. No. 3,709,979, which is also incorporated herein by reference. Zeolite ZSM-12, and the conventional preparation thereof, is described in U.S. Pat. No. 3,832,449, incorporated herein by reference. Zeolite ZSM-23, and the conventional preparation thereof, is described in U.S. Pat. No. 4,076,842, incorporated herein by reference. Zeolite ZSM-35, and the conventional preparation thereof, is described in U.S. Pat. No. 4,016,245, incorporated herein by reference. Another preparation of ZSM-35 is described in U.S. Pat. No. 4,107,195, the disclosure of which is incorporated herein by reference. ZSM-48, and the conventional preparation thereof, is taught by U.S. Pat. No. 4,375,573, incorporated herein by reference. Other examples of zeolite catalysts are described in U.S. Pat. Nos. 5,019,663 and 7,022,888, also incorporated herein by reference. An exemplary condensation catalyst is a ZSM-5 zeolite modified with Cu, Pd, Ag, Pt, Ru, Re, Ni, Sn, or combinations thereof.

As described in U.S. Pat. No. 7,022,888, the condensation catalyst may be a bifunctional pentasil zeolite catalyst including at least one metallic element from the group of Cu, Ag, Au, Pt, Ni, Fe, Co, Ru, Zn, Cd, In, Rh, Pd, Ir, Re, Mn, Cr, Mo, W, Sn, Os, alloys and combinations thereof, or a modifier from the group of In, Zn, Fe, Mo, Au, Ag, Y, Sc, Ni, P, Ta, lanthanides, and combinations thereof. The zeolite may have strong acidic sites, and may be used with reactant streams containing an oxygenated hydrocarbon at a temperature of below 580° C. The bifunctional pentasil zeolite may have ZSM-5, ZSM-8 or ZSM-11 type crystal structure consisting of a large number of 5-membered oxygen-rings (i.e., pentasil rings). In one embodiment the zeolite will have a ZSM-5 type structure.

Alternatively, solid acid catalysts such as alumina modified with phosphates, chloride, silica, and other acidic oxides may be used in the process. Also, sulfated zirconia, phosphated zirconia, titania zirconia, or tungstated zirconia may provide the necessary acidity. Re and Pt/Re catalysts are also useful for promoting condensation of oxygenates to $C_{5+}$ hydrocarbons and/or $C_{5+}$ mono-oxygenates. The Re is sufficiently acidic to promote acid-catalyzed condensation. In certain embodiments, acidity may also be added to activated carbon by the addition of either sulfates or phosphates.

The specific $C_{4+}$ compounds produced will depend on various factors, including, without limitation, the type of oxygenated compounds in the reactant stream, condensation temperature, condensation pressure, the reactivity of the catalyst, and the flow rate of the reactant stream as it affects the space velocity, GHSV, LHSV, and WHSV. In certain embodiments, the reactant stream is contacted with the condensation catalyst at a WHSV that is appropriate to produce the desired hydrocarbon products. In one embodiment the WHSV is at least 0.1 grams of volatile ($C_{2+}$ $O_{1-3}$) oxygenates in the reactant stream per gram catalyst per hour. In another embodiment the WHSV is between 0.1 to 10.0 g/g hr, including a WHSV of 1, 2, 3, 4, 5, 6, 7, 8, 9, 10 g/g hr, and increments between.

In certain embodiments the condensation reaction is carried out at a temperature and pressure at which the thermodynamics of the proposed reaction are favorable. For volatile $C_{2+}$ $O_{1-3}$ oxygenates the reaction may be carried out at a temperature where the vapor pressure of the volatile oxygenates is at least 0.1 atm (and preferably a good deal higher). The condensation temperature will vary depending upon the specific composition of the oxygenated compounds. The condensation temperature will generally be greater than 80° C., or 100° C., or 125° C., or 150° C., or 175° C., or 200° C., or 225° C., or 250° C., and less than 500° C., or 450° C., or 425° C., or 375° C., or 325° C., or 275° C. For example, the condensation temperature may be between 80° C. to 500° C., or between 125° C. to 450° C., or between 250° C. to 425° C. The condensation pressure will generally be greater than 0 psig, or 10 psig, or 100 psig, or 200 psig, and less than 2000 psig, or 1800 psig or, or 1600 psig, or 1500 psig, or 1400 psig, or 1300 psig, or 1200 psig, or 1100 psig, or 1000 psig, or 900 psig, or 700 psig. For example, the condensation pressure may be greater than 0.1 atm, or between 0 and 1500 psig, or between 0 and 1200 psig.

The condensation reactions of the present disclosure can be used in the production of $C_{4+}$ alkanes, $C_{4+}$ alkenes, $C_{5+}$ cycloalkanes, $C_{5+}$ cycloalkenes, aryls, fused aryls, polycyclic compounds, $C_{4+}$ alcohols, $C_{4+}$ ketones, $C_{4+}$ furans and mixtures thereof, with an advantageously high proportion of aryls and a low proportion of alkanes. In particular, the use of the above described mixture of oxygenates results in an aryl yield greater than or equal to 50% carbon fraction (CF) of the aqueous feedstock carbon and a $C_{4+}$ alkane yield less than or equal to 20% CF of the aqueous feedstock carbon. In certain embodiments, the aryls yield can be greater than or equal to 55 wt %, greater than or equal to 60% CF, or greater than or equal to 65% CF of the aqueous feedstock carbon. In certain embodiments, the $C_{4+}$ alkane yield is less than or equal to 15% CF, less than or equal to 10% CF, or less than or equal to 5% CF of the aqueous feedstock carbon. In certain other embodiments, the product may further comprise $C_1$-3 alkanes with the total $C_{1+}$ alkane yield less than or equal to 20% CF, less than or equal to 15% CF, less than or equal to 10% CF, or less than or equal to 5% CF of the aqueous feedstock carbon.

As used herein, the term "carbon fraction" and "CF," which may be used interchangeably, can be calculated by dividing the mass of carbon of the component (e.g., mass of carbon in the aryls) by the mass of carbon in the feed and multiplying by 100. Alternatively, the % CF may be reported as percentage of feed carbon, percentage of carbon in, or other similar nomenclature.

In certain embodiments, the aryls yield is greater than or equal to 55% CF of the aqueous feedstock carbon and the $C_{4+}$ alkane yield is less than or equal to 15% CF of the aqueous feedstock carbon. In another embodiment the aryls yield is greater than or equal to 60% CF of the aqueous feedstock carbon and the $C_{4+}$ alkane yield is less than or equal to 10% CF of the aqueous feedstock carbon. In further embodiments, the aryls yield is greater than or equal to 55% CF of the aqueous feedstock carbon and the $C_{1+}$ alkane yield is less than or equal to 15% CF of the aqueous feedstock carbon. In yet other embodiments, the aryls yield is greater than or equal to 60% CF of the aqueous feedstock carbon and the $C_{1+}$ alkane yield is less than or equal to 10% CF of the aqueous feedstock carbon.

The $C_{4+}$ alkanes and $C_{4+}$ alkenes have from 4 to 30 carbon atoms ($C_{4+}$ alkanes and $C_{4+}$ alkenes) and may be branched or straight chained alkanes or alkenes. The $C_{4+}$ alkanes and $C_{4+}$ alkenes may also include fractions of $C_4$-9, $C_{7-14}$, $C_{12-24}$ alkanes and alkenes, respectively, with the $C_4$-9 fraction directed to gasoline, the $C_{7-16}$ fraction directed to jet fuels, and the $C_{11-24}$ fraction directed to diesel fuel and other industrial applications, such as chemicals. Examples of various $C_{4+}$ alkanes and $C_{4+}$ alkenes include, without limitation, butane, butene, pentane, pentene, 2-methylbutane, hexane, hexene, 2-methylpentane, 3-methylpentane, 2,2-dimethylbutane, 2,3-dimethylbutane, heptane, heptene, octane, octene, 2,2,4,-trimethylpentane, 2,3-dimethyl hexane, 2,3,4-trimethylpentane, 2,3-dimethylpentane, nonane, nonene, decane, decene, undecane, undecene, dodecane, dodecene, tridecane, tridecene, tetradecane, tetradecene, pentadecane, pentadecene, hexadecane, hexadecene, heptyldecane, heptyldecene, octyldecane, octyldecene, nonyldecane, nonyldecene, eicosane, eicosene, uneicosane, uneicosene, doeicosane, doeicosene, trieicosane, trieicosene, tetraeicosane, tetraeicosene, and isomers thereof.

The $C_{5+}$ cycloalkanes and $C_{5+}$ cycloalkenes have from 5 to 30 carbon atoms and may be unsubstituted, mono-substituted or multi-substituted. In the case of mono-substituted and multi-substituted compounds, the substituted group may include a branched $C_{3+}$ alkyl, a straight chain $C_{1+}$ alkyl, a branched $C_{3+}$ alkylene, a straight chain $C_{2+}$ alkylene, a phenyl or a combination thereof. By way of example, at least one of the substituted groups include a branched $C_{3-12}$ alkyl, a straight chain $C_{1-12}$ alkyl, a branched $C_{3-12}$ alkylene, a straight chain $C_{1-12}$ alkylene, a straight chain $C_{2-12}$ alkylene, a phenyl or a combination thereof. By way of further example, at least one of the substituted groups include a branched $C_{3-4}$ alkyl, a straight chain $C_{1-4}$ alkyl, a branched $C_{1-4}$ alkylene, straight chain $C_{1-4}$ alkylene, straight chain $C_{2-4}$ alkylene, a phenyl or a combination thereof. Examples of desirable $C_{5+}$ cycloalkanes and $C_{5+}$ cycloalkenes include, without limitation, cyclopentane, cyclopentene, cyclohexane, cyclohexene, methyl-cyclopentane, methyl-cyclopentene, ethyl-cyclopentane, ethyl-cyclopentene, ethyl-cyclohexane, ethyl-cyclohexene, propyl-cyclohexane, butyl-cyclopentane, butyl-cyclohexane, pentyl-cyclopentane, pentyl-cyclohexane, hexyl-cyclopentane, hexyl-cyclohexane, and isomers thereof.

Aryls will generally consist of an aromatic hydrocarbon in either an unsubstituted (phenyl), mono-substituted or multi-substituted form. In the case of mono-substituted and multi-substituted compounds, the substituted group may include a branched $C_{3+}$ alkyl, a straight chain $C_{1+}$ alkyl, a branched $C_{3+}$ alkylene, a straight chain $C_{2+}$ alkylene, a phenyl or a combination thereof. By way of example, at least one of the substituted groups include a branched $C_{3+}$ alkyl, a straight chain $C_{1-12}$ alkyl, a branched $C_{3-12}$ alkylene, a straight chain $C_{2-12}$ alkylene, a phenyl or a combination thereof. By way of further example, at least one of the substituted groups include a branched $C_{3-4}$ alkyl, a straight chain $C_{1-4}$ alkyl, a branched $C_{3-4}$ alkylene, straight chain $C_{2-4}$ alkylene, a phenyl or a combination thereof. Examples of various aryls include, without limitation, benzene, toluene, xylene (dimethylbenzene), ethyl benzene, para xylene, meta xylene, ortho xylene, $C_{9+}$ aromatics, butyl benzene, pentyl benzene, hexyl benzene, heptyl benzene, octyl benzene, nonyl benzene, decyl benzene, undecyl benzene, and isomers thereof.

Fused aryls will generally consist of bicyclic and polycyclic aromatic hydrocarbons, in either an unsubstituted, mono-substituted, or multi-substituted form. In the case of mono-substituted and multi-substituted compounds, the substituted group may include a branched $C_{3+}$ alkyl, a straight chain $C_{1+}$ alkyl, a branched $C_{3+}$ alkylene, a straight chain $C_{2+}$ alkylene, a phenyl or a combination thereof. By way of example, at least one of the substituted groups include a branched $C_{3-4}$ alkyl, a straight chain $C_{1-4}$ alkyl, a branched $C_{3-4}$ alkylene, straight chain $C_{2-4}$ alkylene, a phenyl or a combination thereof. Examples of various fused aryls include, without limitation, naphthalene, anthracene, and isomers thereof.

Polycyclic compounds will generally consist of bicyclic and polycyclic hydrocarbons, in either an unsubstituted, mono-substituted, or multi-substituted form. Although polycyclic compounds generally include fused aryls, as used herein the polycyclic compounds generally have at least one saturated or partially saturated ring. In the case of mono-substituted and multi-substituted compounds, the substituted group may include a branched $C_{3+}$ alkyl, a straight chain $C_{1+}$ alkyl, a branched $C_{3+}$ alkylene, a straight chain $C_{2+}$ alkylene, a phenyl or a combination thereof. By way of example, at least one of the substituted groups include a branched $C_{3-4}$ alkyl, a straight chain $C_{1-4}$ alkyl, a branched $C_{3-4}$ alkylene, straight chain $C_{2-4}$ alkylene, a phenyl or a combination thereof. Examples of various fused aryls include, without limitation, tetrahydronaphthalene and decahydronaphthalene, and isomers thereof.

The $C_{4+}$ alcohols may also be cyclic, branched or straight chained, and have from 4 to 30 carbon atoms. In general, the $C_{4+}$ alcohols may be a compound according to the formula $R^1$—OH, wherein $R^1$ is a member selected from a branched $C_{4+}$ alkyl, straight chain $C_{4+}$ alkyl, a branched $C_{4+}$ alkylene, a straight chain $C_{4+}$ alkylene, a substituted $C_{5+}$ cycloalkane, an unsubstituted $C_{5+}$ cycloalkane, a substituted $C_{5+}$ cycloalkene, an unsubstituted $C_{5+}$ cycloalkene, an aryl, a phenyl or combinations thereof. Examples of desirable $C_{4+}$ alcohols include, without limitation, butanol, pentanol, hexanol, heptanol, octanol, nonanol, decanol, undecanol, dodecanol, tridecanol, tetradecanol, pentadecanol, hexadecanol, heptyldecanol, octyldecanol, nonyldecanol, eicosanol, uneicosanol, doeicosanol, trieicosanol, tetraeicosanol, or isomers thereof.

The $C_{4+}$ ketones may also be cyclic, branched or straight chained, and have from 4 to 30 carbon atoms. In general, the $C_{4+}$ ketone may be a compound according to the formula

wherein $R^3$ and $R^4$ are independently a member selected from a branched $C_{3+}$ alkyl, a straight chain $C_{1+}$ alkyl, a branched $C_{3+}$ alkylene, a straight chain $C_{2+}$ alkylene, a substituted $C_{8+}$ cycloalkane, an unsubstituted $C_{5+}$ cycloalkane, a substituted $C_{5+}$ cycloalkene, an unsubstituted $C_{5+}$ cycloalkene, an aryl, a phenyl or a combination thereof. Examples of desirable $C_{4+}$ ketones include, without limitation, butanone, pentanone, hexanone, heptanone, octanone, nonanone, decanone, undecanone, dodecanone, tridecanone, tetradecanone, pentadecanone, hexadecanone, heptyldecanone, octyldecanone, nonyldecanone, eicosanone, uneicosanone, doeicosanone, trieicosanone, tetraeicosanone, or isomers thereof.

In some embodiments, the condensation product stream 124 comprising $C_{4+}$ compounds can be fractionated into various product streams, such as gasoline, jet fuel (kerosene), diesel fuel, and aromatics. The condensation product stream 124 may be passed through a three-phase separator 126 to separate the condensation product stream 124 into an acid condensation gas stream 128, an organic stream 130, and an aqueous stream 132. The organic stream 130 and aqueous stream 132 are separated by density difference, while the acid condensation gas stream 128 comprising uncondensed gases is recycled to the acid condensation reactor 120 to generate additional $C_{4+}$ compounds. In some embodiments, a gas transport device, such as a blower or compressor, is configured in the acid condensation gas stream 128 to control the recycle pressure. In some embodiments, an optional purge stream 134 may also be used to control the pressure of the recycle loop in the acid condensation gas stream 128. In some embodiments, the aqueous stream 132 is discarded from the process, or further processed in downstream process units.

In some embodiments, the organics stream 130 is fractionated in a distillation column 136 to separate the organic stream 130 into a light product stream 138 and a heavy product stream 140. In some embodiments, the distillation unit 136 is configured to remove co-boiling contaminants for benzene, toluene, or a combination thereof. As described, removing co-boiling contaminants for benzene and/or toluene prior to processing over a transalkylation and/or dealkylation catalyst 22 offers various surprising and unexpected advantages, such as a higher purity and yield of desired aromatic products.

In some embodiments, the distillation column 136 is configured to generate a heavy stream 140 that is free or substantially free of co-boiling non-aromatic contaminants for benzene. The distillation column 136 may remove co-boiling nonaromatic contaminants for benzene by fractionating the organic stream 130 into a $C_{6-}$ stream comprising benzene, co-boiling non-aromatic contaminants for benzene, and lighter products through the light product stream 138. The distillation column 136 may further fractionate the organic stream 130 into a heavy product stream 140 comprising $C_{7+}$ compounds.

In some embodiments, the distillation column 136 is configured to generate a heavy stream 140 that is free or substantially free of co-boiling nonaromatic contaminants for toluene. The distillation column 136 may remove co-boiling nonaromatic contaminants for toluene by fractionating the organic stream 130 into a $C_{7-}$ or $C_{8-}$ stream comprising toluene, co-boiling nonaromatic contaminants for toluene, and lighter products through the light product stream 138. The distillation column 136 may further fractionate the organic stream 130 into a heavy product stream 140 comprising $C_{8+}$ or $C_{9+}$ compounds.

In some embodiments, the heavy product stream 140 is fractionated in a distillation column 142 to separate the heavy product stream 140 comprising $C_{7+}$ compounds, $C_{8+}$ compounds, or $C_{9+}$ compounds into the mixed aromatic feed stream 16 and a heavy product stream 146. In some embodiments, the distillation column 142 is configured to fractionate the heavy product stream 140 into a mixed aromatic feed stream 16 comprising $C_{7+}$ compounds and a heavy product feed stream 144 comprising $C_{11+}$ compounds. In some embodiments, the mixed aromatic feed stream 16 comprises $C_{7+}$ compounds, or $C_{8+}$ compounds, or $C_{9+}$ compounds, or $C_{7-10}$ compounds, or $C_{8-10}$ compounds, or $C_{9-10}$ compounds. The mixed aromatic feed stream 16 may be utilized as the inlet feed for the process described in FIG. 1.

In some embodiments, the heavy stream 144 may be further separated for use as kerosene (e.g., $C_{11-14}$ as jet fuel use), diesel fuel use (e.g., $C_{12-24}$), and lubricants or fuel oils (e.g., $C_{25+}$). Alternatively, the heavy stream 144 may be cracked to produce addition fractions for use in gasoline, kerosene, aromatics, and/or diesel fractions.

Unless defined otherwise, all technical and scientific terms used herein have the same meaning as commonly understood by one of ordinary skill in the art to which the invention pertains. All definitions, as defined and used herein, should be understood to control over dictionary definitions, definitions in documents incorporated by reference, and/or ordinary meanings of the defined terms.

The present invention has been described in terms of one or more preferred embodiments, and it should be appreciated that many equivalents, alternatives, variations, and modifications, aside from those expressly stated, are possible and within the scope of the invention.

EXAMPLES

The following examples will enable one of skill in the art to more readily understand the principles of the present disclosure. The following examples are presented by way of illustration and are not meant to be limiting in any way.

Inventive Example 1: Production of High Purity Aromatics from a Mixed Aromatic Feed A mixed aromatic feed stream (MAF) containing $C_7$-$C_{10}$ aromatics, and lacking substantial benzene co-boiling nonaromatic contaminants, was processed across a nickel containing ZSM-5 catalyst at 375° C., 100 psig, with a hydrogen to hydrocarbon ratio of approximately 4, and at a weight hourly space velocity of 1. While the feed contained less than 0.1% of benzene, the product contained 7.04 wt % benzene, based on the total weight of the product stream. The potential purity of the benzene is estimated by dividing the amount of benzene by the total of the benzene co-boiling materials (including benzene) and multiplying by 100. The benzene co-boiling range is defined here as all components (including benzene) with retention times greater than, and including methylcyclopentane (normal boiling point 71.8° C.) and less than, and including 1,3 dimethylcyclopentane, cis (boiling point 91° C.) as measured by gas chromatograph (GC). The estimated benzene purity in the product was 99.8 wt %. Because the feed did not contain substantial benzene, the purity of the benzene in the feed could not be estimated.

Comparative Example 1: Production of Benzene from a Mixed Aromatic Feed Containing Co-Boiling Contaminants A MAF containing $C_4$-$C_{10}$ aromatics, and containing substantial benzene co-boiling non-aromatic contaminants was processed under the same conditions as Example 1. The estimated benzene purity in the product was 98%. While this is substantially higher than the estimated benzene purity of the feed, 31%, there are still approximately 10× the benzene co-boiling contaminants present in the Example 2 product compared to the Example 1 product, illustrating the advantage of eliminating the co-boiling contaminants in the feed.

Inventive Example 2: Production of High Purity Aromatics from a Mixed Aromatic Feed Stream A MAF containing $C_9$-$C_{10}$ aromatics, and lacking substantial benzene or toluene co-boiling non-aromatic contaminants was processed under the same conditions as Example 1 with the exception that the pressure was increased from 200 to 250 psig and a transalkylation catalyst was used. The estimated benzene purity in the product was 99.87%. Using a method similar to that defined for determining benzene purity in example 1, the co-boiling range for toluene is defined here as all components (including toluene) with retention times greater than, and including 1,3 dimethylcyclopentane, cis (boiling point 91° C.) and less than, and including trans 1,2-dimethyl-cyclohexane (boiling point 123° C.) as measured by gas chromatograph (GC). No detectable components other than toluene were found in this boiling point range using this analysis, indicating a toluene estimated purity of nearly 100%.

Comparative Example 2: Production of Aromatics from a Mixed Aromatic Feed Stream Containing Co-Boiling Contaminants A MAF was produced. The raw hydrocarbon product of the production process was subjected to a distillation step to remove heavy components, generally containing eleven or more carbon atoms. The resulting $C_4$-$C_{10}$ MAF generated lower yields of aromatics is not suitable for use with this invention.

Inventive Example 3: Production of High Purity Aromatics from a Mixed Aromatic Feed Stream A MAF was produced. The raw hydrocarbon product of the production process was subjected to two distillation steps. In the first step, the raw hydrocarbons were distilled to produce an overhead product containing components primarily containing six or fewer carbon atoms, including benzene. The overhead product was recycled to the aromatization section. Surprisingly, by recycling the light product to the reaction section, the total yield of aromatics increased. The dehexanized aromatics were then distilled to remove heavy components, generally containing eleven or more carbon atoms. The resulting $C_7$-$C_{10}$ MAF is suitable for use with this invention to produce pure benzene.

Inventive Example 4: Production of MAF from an Aqueous Hydrocarbon Stream

An aqueous mixture of oxygenates was processed across a nickel containing ZSM-5 condensation catalyst at 375° C., 150 psig, and at a weight hourly space velocity of 0.5. The resultant condensation product was fractionated into a light stream and heavy stream, where the light stream was composed of $C_3$-$C_6$ components that were recycled back to the condensation catalyst. The heavy stream was fractionated to produce a MAF of primarily $C_7$-$C_{10}$ aromatics. A representative MAF product is shown in Table 1.

TABLE 1

| Component | wt % |
|---|---|
| Benzene | 1.21 |
| Toluene | 16.35 |
| Ethyl benzene | 2.21 |
| m-Xylene | 16.94 |
| p-Xylene | |
| o-Xylene | 5.2 |
| C9 Aromatics | 40.38 |
| C10 Aromatics | 11.97 |
| C11+ Aromatics | 2.15 |
| Total Aromatics | 96.41 |
| Light products | 0.57 |
| non aromatics B-T | 1.42 |
| non aromatics T-E | 1.27 |
| non aromatics E-9 | 0.34 |
| Total non-aromatics | 3.6 |

Inventive Example 5: Production of Mixed Xylenes from a Mixed Aromatic Feed

The MAF from Example 4 containing substantial xylene co-boiling non-aromatic contaminants was processed across a transalkylation catalyst at 344° C., 430 psig, with a hydrogen to hydrocarbon ratio of approximately 3.8, and at a weight hourly space velocity of 3.3. The product was fractionated into benzene rich, toluene rich, xylene rich, $C_9$ aromatic rich, and $C_{10+}$ aromatic rich streams, as shown in Table 2. The toluene and $C_9$ aromatic streams were recycled back to the translkylation catalyst to maximize xylenes production. The xylene rich stream was sent to an isomer-recovery process unit to produce a para-xylene isomer stream and a raffinate stream comprising non-recovered $C_8$ compounds. The raffinate stream was processed across an isomerization catalyst at 340° C., 150 psig, with a hydrogen to hydrocarbon ratio of approximately 1.5, and at a weight hourly space velocity of 3.3. An isomerization product stream was produced, which was then combined with the xylene stream and sent back again to the isomer-recovery process unit. This continued operation led to a production rate of >99.7% para-xylene from the isomer-recovery process unit of 457 kilograms per month.

TABLE 2

| Stream | MAF | Benzene | Toluene | $C_9$ | $C_{10+}$ | Xylenes | Xylene Raffinate | Isomerization Product |
|---|---|---|---|---|---|---|---|---|
| Flow rate (g/min) | 26.9 | 3.7 | 9.2 | 14.5 | 1.2 | 103.5 | 86.9 | 86.9 |
| Benzene (wt %) | 1.21 | 81.08 | | | | 0 | 0.08 | 1.34 |
| Toluene (wt %) | 16.35 | 0.05 | 99.09 | | | 4.05 | 1.46 | 0.55 |
| Ethyl benzene (wt %) | 2.21 | | 0.03 | 0.02 | | 4.13 | 3.56 | 4.21 |
| m-Xylene (wt %) | 16.94 | | 0.16 | 1.34 | | 47.23 | 57.38 | 50.03 |
| p-Xylene (wt %) | | | | | | 20.79 | 12.37 | 21.87 |
| o-Xylene (wt %) | 5.2 | | 0 | 4.94 | | 19.47 | 24.12 | 20.98 |
| C9 Aromatics (wt %) | 40.38 | | | 74.33 | | 3.7 | 0.84 | 0.45 |
| C10 Aromatics (wt %) | 11.97 | | | 19.34 | 46.26 | 0.51 | 0.04 | 0.26 |
| C11+ Aromatics (wt %) | 2.15 | | | | 53.73 | | | |
| Total Aromatics (wt %) | 96.41 | 81.13 | 99.28 | 99.97 | 99.99 | 99.88 | 99.85 | 99.69 |
| Light Products (wt %) | 0.57 | 17.74 | 0.01 | 0.01 | 0.01 | | | |
| non aromatics B-T (wt %) * | 1.42 | 1.14 | 0.19 | | | | | |
| non aromatics T-E (wt %) * | 1.27 | | 0.52 | | | | | |
| non aromatics E-9 (wt %) * | 0.34 | | | 0.01 | | | | |
| Total non-aromatics (wt %) | 3.6 | 18.88 | 0.72 | 0.02 | 0.01 | 0.12 | 0.15 | 0.31 |

* Non-aromatic components that boil between benzene and toluene (B-T), between toluene and ethyl benzene (T-E), and between ethyl benzene and C9 aromatic (E-9).

Inventive Example 6: Production of Benzene from a Mixed Aromatic Feed

A benzene rich stream produced in the same manner as Example 4 was further processed over a transalkylation catalyst at 375° C., 40 psig, with a hydrogen to hydrocarbon ratio of approximately 0.4, and at a weight hourly space velocity of 1. The product stream was fractionated to recover a purified benzene stream of >99.9% purity with the product composition shown in Table 3.

TABLE 3

| Component | Result (wt %) |
|---|---|
| Benzene Purity | 99.93 |
| Toluene | 0.07 |
| C8+ Aromatics | <0.01 |
| 1,4-Dioxane | <0.01 |
| Non-Aromatics | <0.01 |

Inventive Example 7: Production of Toluene from a Mixed Aromatic Feed

A toluene rich stream was produced in the same manner as Example 4 with more optimized fractionation conditions to achieve 99.8% toluene purity. Rather than being recycled back to transalkylation to maximize xylene production, the toluene rich stream was recovered as a product with the composition as shown in Table 4.

TABLE 4

| Component | Result (wt %) |
|---|---|
| Toluene | 99.80 |
| Benzene | 0.00 |
| Ethylbenzene | 0.01 |
| Xylenes | 0.16 |
| Non-Aromatics | 0.03 |

Inventive Example 8: Production of High Purity Para-Xylene from a Mixed Aromatic Feed A MAF containing $C_5$-$C_{10}$ aromatics, and containing substantial xylene co-boiling non-aromatic contaminants, was fractioned to remove $C_5$-$C_6$ compounds. The resulting MAF containing $C_7$-$C_{10}$ aromatics was processed across a transalkylation catalyst at 360° C., 430 psig, with a hydrogen to hydrocarbon ratio of approximately 3.6, and at a weight hourly space velocity of 2.7. Production of para-xylene was increased by bypassing a portion of the isomerization product stream around the fractionation and combining it with the $C_8$ stream prior to entering the isomer-recovery process unit. 150 grams per minute was bypassed, and 20 grams per minute was put through the fractionation. The resulting para-xylene production increased from 457 kilograms per month to 830 kilograms per month. The composition of a representative para-xylene product is shown in Table 5, and the results from different processes are shown in Table 6.

TABLE 5

| Component | Result (wt %) |
|---|---|
| para-Xylene | 99.93 |
| Toluene | 0.02 |
| o-Xylene | 0.01 |
| m-Xylene | 0.03 |
| Ethylbenzene | <0.01 |
| Non-Aromatics | <0.01 |

TABLE 6

| | Bypass Used | >99.7% para-Xylene (kg/month) |
|---|---|---|
| Example 5 | No | 457 |
| Example 8 | Yes | 830 |

Although the invention has been described in considerable detail with reference to certain embodiments, one skilled in the art will appreciate that the present invention can be used in alternative embodiments to those described, which have been presented for purposes of illustration and not of limitation. Therefore, the scope of the appended claims should not be limited to the description of the embodiments contained herein.

For reasons of completeness, various aspects of the invention are set out in the following numbered clauses:

Clause 1. A method for separating an aromatic compound from a mixed aromatic feed stream, the method comprising:

(i) contacting a mixed aromatic feed stream comprising $C_{7-10}$ aromatic hydrocarbons with an aromatics processing catalyst to produce a product stream,
wherein the aromatics processing catalyst comprises a transalkylation catalyst, a dealkylation catalyst, a hydrocracking catalyst, or a combination thereof,
wherein the mixed aromatic feed stream comprises greater than 1 wt % of non-aromatic components based on the total weight of the mixed aromatic feed stream, and wherein the mixed aromatic feed stream is substantially free of $C_{12+}$ aromatics; and
(ii) fractionating the product stream to separate an aromatic compound from the product stream.

Clause 2. The method of clause 1, wherein the mixed aromatic feed stream comprises from 0.1 wt % to 45 wt % olefins, based on the total weight of the mixed aromatic feed stream.

Clause 3. The method of clause 1, wherein the mixed aromatic feed stream comprises from 0.1 wt % to 25 wt % napthenes, based on the total weight of the mixed aromatic feed stream.

Clause 4. The method of clause 1, wherein the mixed aromatic feed stream comprises from 0.1 wt % to 40 wt % naptheno-olefins, based on the total weight of the mixed aromatic feed stream.

Clause 5. The method of clause 1, wherein the mixed aromatic feed stream has a bromine number of at least 1 mg $Br_2$/g of the mixed aromatic feed to less than 100 mg $Br_2$/g of the mixed aromatic feed.

Clause 6. The method of clause 1, wherein the mixed aromatic feed stream comprises phenols in an amount from 10 ppm to 10 wt %, based on the total weight of the mixed aromatic feed stream.

Clause 7. The method of clause 1, wherein the mixed aromatic feed comprises oxygenates in an amount from 10 ppm to 10 wt % ppm, based on the total weight of the mixed aromatic feed stream.

Clause 8. The method of clause 1, wherein the $C_{7-10}$ aromatic hydrocarbon comprises benzene, toluene, a xylene, a trimethyl benzene, a tetramethyl benzene, naphthalene, or combinations thereof.

Clause 9. The method of clause 1, wherein step (ii) further includes fractionating the product stream to separate a $C_8$ stream from the product stream of step (i); and
the method further comprises
(iii) subjecting at least a portion of the $C_8$ stream to an isomer-recovery process unit to produce a xylene isomer stream and a raffinate stream comprising non-recovered $C_8$ compounds; and
(iv) contacting the raffinate stream with an isomerization catalyst to produce an isomerization product stream, wherein the isomerization product stream comprises at least one xylene isomer, and wherein at least a portion of the isomerization product stream is combined with the product stream produced from the aromatics processing catalyst in step (i).

Clause 10. The method of clause 1, wherein the mixed aromatic feed stream comprises $C_{9-10}$ aromatics.

Clause 11. The method of clause 9, wherein at least a portion of the isomerization product stream is recycled and combined with the $C_8$ stream entering the isomer-recovery process unit.

Clause 12. The method of clause 1, wherein the mixed aromatic feed steam is free of co-boiling contaminants for benzene, toluene, and a combination thereof.

Clause 13. The method of clause 1, wherein step (ii) further comprises feeding the product stream comprising the $C_8$ aromatics to a first distillation column that fractionates the product stream to separate a $C_{7-}$ stream from a $C_{8+}$ stream.

Clause 14. The method of clause 13, wherein the $C_{7-}$ stream is fed to a second distillation column that fractionates the $C_{7-}$ stream into a $C_{6-}$ stream and a $C_7$ stream.

Clause 15. The method of clause 14, wherein at least a portion of the $C_7$ stream is recycled and combined with the mixed aromatic feed stream.

Clause 16. The method of clause 9, wherein at least a portion of the $C_{8+}$ stream is recycled and combined with the $C_8$ aromatics entering the isomer-recovery process unit.

Clause 17. The method of clause 13, wherein step (ii) further comprises feeding the $C_{8+}$ stream to a third distillation column that fractionates the $C_{8+}$ stream into a $C_8$ stream and a $C_{9+}$ stream, wherein the $C_8$ stream comprises the $C_8$ aromatics.

Clause 18. The method of clause 17, wherein the $C_{9+}$ stream is fed to a fourth distillation column that fractionates the $C_{9+}$ stream into a $C_{9-10}$ stream and a $C_{11+}$ stream, wherein the $C_{9-10}$ stream is recycled and combined with the mixed aromatic feed stream.

Clause 19. The method of clause 9, wherein step (ii) further comprises fractionating the product stream to separate a $C_7$ stream, a $C_8$ stream, and a $C_{9-10}$ stream, wherein the $C_8$ stream is fed to the isomer-recovery process unit, the $C_7$ stream is recycled and combined with the mixed aromatic feed stream, and the $C_{9-10}$ stream is recycled and combined with the mixed aromatic feed stream.

Clause 20. The method of clause 9, wherein step (ii) further comprises fractionating the product stream to separate a $C_7$ stream, a $C_8$ stream, and a $C_{9+}$ stream, wherein the $C_8$ stream is fed to the isomer-recovery process unit, the $C_7$ stream is recycled and combined with the mixed aromatic feed stream, and the $C_{9+}$ stream is recovered as a product.

Clause 21. The method of clause 9, wherein the isomer-recovery process unit comprises an adsorption unit.

Clause 22. The method of clause 9, wherein the isomer-recovery process unit comprises a crystallization unit.

Clause 23. The method of clause 1, wherein the aromatics processing catalyst comprises an acid catalyst.

Clause 24. The method of clause 23, wherein the acid catalyst is selected from aluminosilicates, tungstated aluminosilicates, silica-alumina phosphates, aluminum phosphates, amorphous silica alumina, zirconia, sulfated zirconia, tungstated zirconia, tungsten carbide, molybdenum carbide, titania, acidic alumina, phosphated alumina, tungstated alumina, phosphated silica, tungstated silica, tungstated titania, tungstated phosphate, niobia, sulfated carbons, phosphated carbons, acidic resins, heteropolyacids, tungstated heteropolyacid, inorganic acids or combinations thereof.

Clause 25. The method of clause 23, wherein the acid catalyst includes a metal selected from Cu, Ag, Au, Pt, Ni, Fe, Co, Ru, Rh, Zn, Ga, In, Pd, Ir, Re, Mn, Cr, Mo, W, Sn, Os, alloys or combinations thereof.

Clause 26. The method of clause 1, wherein step (i) occurs at a temperature from 200° C. to 600° C.

Clause 27. The method of clause 1, wherein step (i) occurs at a pressure from 100 psig to 1500 psig.

Clause 28. The method of clause 1, wherein step (i) occurs at a weight hourly space velocity (WHSV) from 0.1 to 10 mass feed/mass catalyst/hour.

Clause 29. The method of clause 1, wherein step (i) includes feeding hydrogen in an amount of at least 0.1 mol of hydrogen per mol of mixed aromatic feed.

Clause 30. The method of clause 1, wherein step (1) includes feeding hydrogen in an amount of at least 1 mol of hydrogen per mol of mixed aromatic feed.

Clause 31. A method for producing and separating an aromatic compound from a mixed aromatic feed stream, the method comprising:
(i) contacting an aqueous hydrocarbon feedstock comprising water and one or more oxygenate with a condensation catalyst to produce a condensation product stream comprising $C_{4+}$ compounds, wherein the $C_{4+}$ compounds comprises a $C_{4+}$ alcohol, a $C_{4+}$ ketone, a $C_{4+}$ alkane, a $C_{4+}$ alkene, a $C_{5+}$ cycloalkane, a $C_{5+}$ cycloalkene, an aryl, or a fused aryl;
(ii) fractionating the condensation product stream to generate a light stream and a heavy stream, wherein the light stream comprises co-boiling non-aromatic contaminants for benzene or toluene, and the heavy stream is substantially free of co-boiling non-aromatic contaminants for benzene or toluene;
(iii) recycling the light stream to the condensation catalyst;
(iv) fractionating the heavy stream into a mixed aromatic feed comprising $C_{7+}$ aromatics; and
(v) contacting the mixed aromatic feed stream with an aromatics processing catalyst to produce a product stream, wherein the aromatics processing catalyst comprises a transalkylation catalyst, a dealkylation catalyst, a hydrocracking catalyst, or a combination thereof.

Clause 32. The method of clause 31 further comprising:
fractionating the product stream to separate a $C_8$ stream from the product stream;
subjecting at least a portion of the $C_8$ stream to an isomer-recovery process unit to produce a xylene isomer stream and a raffinate stream comprising non-recovered $C_8$ compounds.
contacting the raffinate stream with an isomerization catalyst to produce an isomerization product stream, wherein the isomerization product stream comprises at least one xylene isomer, wherein at least a portion of the isomerization product stream is combined with the product stream produced from the aromatics processing catalyst.

Clause 33. The method of clause 31 further including fractionating the $C_{7+}$ stream from step (iv) into a $C_{7-10}$ stream and a $C_{11+}$ stream, wherein the $C_{7-10}$ stream is contacted with the aromatics processing catalyst.

Clause 34. The method of clause 31 further including fractionating the $C_{9+}$ stream from step (iv) into a $C_{9-10}$ stream and a $C_{11+}$ stream, wherein the $C_{9-10}$ stream is contacted with the catalyst.

Clause 35. The method of clause 32, wherein at least a portion of the isomerization product stream is recycled and combined with the $C_8$ stream entering the isomer-recovery process unit.

Clause 36. The method of clause 31 further comprising fractionating the product stream from step (v) to generate a benzene stream, a toluene stream, or a naphthalene stream.

Clause 37. The method of clause 32 further comprising feeding the product stream to a first distillation column that fractionates the product stream into a $C_{7-}$ stream from a $C_{8+}$ stream.

Clause 38. The method of clause 37, further comprising feeding the $C_{7-}$ stream to a second distillation column that fractionates the $C_{7-}$ stream into a $C_{6-}$ stream and a $C_7$ stream.

Clause 39. The method of clause 38, wherein at least a portion of the $C_7$ stream is recycled and combined with the $C_{7+}$ stream.

Clause 40. The method of clause 37, wherein at least a portion of the $C_{8+}$ stream is recycled and combined with the $C_8$ aromatics entering the isomer-recovery process unit.

Clause 41. The method of clause 37 further comprising feeding the $C_{8+}$ stream to a third distillation column that fractionates the $C_{8+}$ stream into a $C_8$ stream and a $C_{9+}$ stream, wherein the $C_8$ stream comprises the $C_8$ aromatics.

Clause 42. The method of clause 41, wherein the $C_{9+}$ stream is fed to a fourth distillation column that fractionates the $C_{9+}$ stream into a $C_{9-10}$ stream and a $C_{11+}$ stream, wherein the $C_{9-10}$ stream is recycled and combined with the mixed aromatic feed stream.

Clause 43. The method of clause 32 further comprising fractionating the product stream to separate a $C_7$ stream, a $C_8$ stream, and a $C_{9-10}$ stream, wherein the $C_8$ stream is fed to the isomer-recovery process unit, the $C_7$ stream is recycled and combined with $C_{7+}$ stream, and the $C_{9-10}$ stream is recycled and combined with the $C_{7+}$ stream.

Clause 44. The method of clause 32, wherein the isomer-recovery process unit comprises an adsorption unit.

Clause 45. The method of clause 32, wherein the isomer-recovery process unit comprises a crystallization unit.

Clause 46. The method of clause 31, wherein the aromatics processing catalyst comprises an acid catalyst.

Clause 47. The method of clause 31, wherein the acid catalyst is selected from aluminosilicates, tungstated aluminosilicates, silica-alumina phosphates, aluminum phosphates, amorphous silica alumina, zirconia, sulfated zirconia, tungstated zirconia, tungsten carbide, molybdenum carbide, titania, acidic alumina, phosphated alumina, tungstated alumina, phosphated silica, tungstated silica, tungstated titania, tungstated phosphate, niobia, sulfated carbons, phosphated carbons, acidic resins, heteropolyacids, tungstated heteropolyacid, inorganic acids and combinations thereof.

Clause 48. The method of clause 47, wherein the acid catalyst includes a metal selected from Cu, Ag, Au, Pt, Ni, Fe, Co, Ru, Rh, Zn, Ga, In, Pd, Ir, Re, Mn, Cr, Mo, W, Sn, Os, alloys and combinations thereof.

Clause 49. The method of clause 31 wherein step (iv) occurs at a temperature from 200° C. to 600° C. and a pressure from 100 psig to 1500 psig and at a weight hourly space velocity (WHSV) from 0.1 to 10 mass feed/mass catalyst/hour.

Clause 50. A method for producing and separating a xylene isomer, the method comprising:
(i) contacting a mixed aromatic feed stream comprising $C_{7+}$ aromatics with an aromatics processing catalyst to produce a product stream comprising an increased concentration of $C_8$ aromatics relative to the mixed aromatic feed stream, wherein the aromatics processing catalyst comprises a transalkylation catalyst, a dealkylation catalyst, a hydrocracking catalyst or a combination thereof;
(ii) fractionating, using a distillation column, the product stream into a $C_{7-}$ stream and a $C_{8+}$ stream;
(iii) fractionating, using a distillation column, the $C_{8+}$ stream into a $C_8$ stream and a $C_{9+}$ stream;
(iv) subjecting at least a portion of the $C_8$ stream to an isomer-recovery process unit to produce a xylene isomer stream and a raffinate stream comprising non-recovered $C_8$ compounds; and (v) contacting the raffinate stream with an isomerization catalyst to produce an isomerization product stream, wherein the isomerization product stream comprises at least one xylene isomer, wherein at least a portion of the $C_{8+}$ stream bypasses the distillation column in step (iii) and is combined with the $C_8$ stream prior to entering the isomer-recovery process unit.

Clause 51. The method of clause 50, wherein the xylene isomer is selected from paraxylene, orthoxylene, or metaxylene.

Clause 52. The method of clause 50, wherein at least a portion of the isomerization product stream is combined with the product stream produced from the catalyst in step (i).

Clause 53. The method of clause 50, wherein the mixed aromatic feed steam is substantially free of co-boiling contaminants for benzene, toluene, and a combination thereof.

Clause 54. The method of clause 50, wherein the $C_{7-}$ stream is fed to a distillation column that fractionates the $C_{7-}$ stream into a $C_{6-}$ stream and a $C_7$ stream.

Clause 55. The method of clause 54, wherein at least a portion of the $C_7$ stream is recycled and combined with the mixed aromatic feed stream.

Clause 56. The method of clause 50, wherein the $C_{9+}$ stream is fed to a distillation column that fractionates the $C_{9+}$ stream into a $C_{9-10}$ stream and a $C_{11+}$ stream, wherein the $C_{9-10}$ stream is recycled and combined with the mixed aromatic feed stream.

Clause 57. The method of clause 50, wherein the isomer-recovery process unit comprises an adsorption unit.

Clause 58. The method of clause 50, wherein the isomer-recovery process unit comprises a crystallization unit.

Clause 59. The method of clause 40, wherein the aromatics processing catalyst comprises an acid catalyst.

Clause 60. The method of clause 59, wherein the acid catalyst is selected from aluminosilicates, tungstated aluminosilicates, silica-alumina phosphates, aluminum phosphates, amorphous silica alumina, zirconia, sulfated zirconia, tungstated zirconia, tungsten carbide, molybdenum carbide, titania, acidic alumina, phosphated alumina, tungstated alumina, phosphated silica, tungstated silica, tungstated titania, tungstated phosphate, niobia, sulfated carbons, phosphated carbons, acidic resins, heteropolyacids, tungstated heteropolyacid, inorganic acids or combinations thereof.

Clause 61. The method of clause 59, wherein the acid catalyst includes a metal selected from Cu, Ag, Au, Pt, Ni, Fe, Co, Ru, Rh, Zn, Ga, In, Pd, Ir, Re, Mn, Cr, Mo, W, Sn, Os, alloys or combinations thereof.

Clause 62. The method of clause 50, wherein step (i) occurs at a temperature from 200° C. to 600° C.

Clause 63. The method of clause 50, wherein step (i) occurs at a pressure from 100 psig to 1500 psig.

Clause 64. The method of clause 50, wherein step (i) occurs at a weight hourly space velocity (WHSV) from 0.1 to 10 mass feed/mass catalyst/hour.

Clause 65. The method of clause 50, wherein prior to step (i) the method includes:

contacting an aqueous hydrocarbon feedstock comprising water and one or more oxygenate with a condensation catalyst to produce a condensation product stream comprising $C_{4+}$ compounds, wherein the $C_{4+}$ compounds comprises a $C_{4+}$ alcohol, a $C_{4+}$ ketone, a $C_{4+}$ alkane, a $C_{4+}$ alkene, a $C_{5+}$ cycloalkane, a $C_{5+}$ cycloalkene, an aryl, or a fused aryl;

fractionating the condensation product stream to separate a $C_{6-}$ stream from a $C_{7+}$ stream;

recycling the $C_{6-}$ stream to the condensation catalyst;

fractionating the $C_{7+}$ stream into a $C_{7-10}$ stream and a $C_{11+}$ stream, wherein the $C_{7-10}$ stream forms the mixed aromatic feed stream.

Clause 66. A method for producing and separating a xylene isomer, the method comprising:

(i) contacting a mixed aromatic feed stream comprising $C_{7+}$ aromatics with an aromatics processing catalyst to produce a product stream comprising an increased concentration of $C_8$ aromatics relative to the mixed aromatic feed stream, wherein the aromatics processing catalyst comprises a transalkylation catalyst, a dealkylation catalyst, a hydrocracking catalyst or a combination thereof;

(ii) fractionating, using a distillation column, the product stream into a $C_{7-}$ stream and a $C_{8+}$ stream;

(iii) fractionating, using a distillation column, the $C_{8+}$ stream into a $C_8$ stream and a $C_{9+}$ stream;

(iv) subjecting at least a portion of the $C_8$ stream to an isomer-recovery process unit to produce a xylene isomer stream and a raffinate stream comprising non-recovered $C_8$ compounds; and (v) contacting the raffinate stream with an isomerization catalyst to produce an isomerization product stream, wherein the isomerization product stream comprises at least one xylene isomer, wherein at least a portion of the isomerization product stream is combined with the $C_8$ stream prior to entering the isomer-recovery process unit.

Clause 67. The method of clause 66, wherein the xylene isomer comprises paraxylene, orthoxylene, or metaxylene.

Clause 68. The method of clause 66, wherein at least a portion of the $C_{8+}$ stream bypasses the distillation column in step (iii) and is combined with the $C_8$ stream prior to entering the isomer-recovery process unit.

Clause 69. The method of clause 66, wherein the mixed aromatic feed steam is substantially free of co-boiling contaminants for benzene, toluene, and a combination thereof.

Clause 70. The method of clause 66, wherein the $C_{7-}$ stream is fed to a distillation column that fractionates the $C_{7-}$ stream into a $C_{6-}$ stream and a $C_7$ stream.

Clause 71. The method of clause 70, wherein at least a portion of the $C_7$ stream is recycled and combined with the mixed aromatic feed stream.

Clause 72. The method of clause 66, wherein the $C_{9+}$ stream is fed to a distillation column that fractionates the $C_{9+}$ stream into a $C_{9-10}$ stream and a $C_{11+}$ stream, wherein the $C_{9-10}$ stream is recycled and combined with the mixed aromatic feed stream.

Clause 73. The method of clause 66, wherein the isomer-recovery process unit comprises an adsorption unit.

Clause 74. The method of clause 66, wherein the isomer-recovery process unit comprises a crystallization unit.

Clause 75. The method of clause 66, wherein the aromatics processing catalyst comprises an acid catalyst.

Clause 76. The method of clause 75, wherein the acid catalyst is selected from aluminosilicates, tungstated aluminosilicates, silica-alumina phosphates, aluminum phosphates, amorphous silica alumina, zirconia, sulfated zirconia, tungstated zirconia, tungsten carbide, molybdenum carbide, titania, acidic alumina, phosphated alumina, tungstated alumina, phosphated silica, tungstated silica, tungstated titania, tungstated phosphate, niobia, sulfated carbons, phosphated carbons, acidic resins, heteropolyacids, tungstated heteropolyacid, inorganic acids or combinations thereof.

Clause 77. The method of clause 75, wherein the acid catalyst includes a metal selected from Cu, Ag, Au, Pt, Ni, Fe, Co, Ru, Rh, Zn, Ga, In, Pd, Ir, Re, Mn, Cr, Mo, W, Sn, Os, alloys or combinations thereof.

Clause 78. The method of clause 66, wherein step (i) occurs at a temperature from 200° C. to 600° C.

Clause 79. The method of clause 66, wherein step (i) occurs at a pressure from 100 psig to 1500 psig.

Clause 80. The method of clause 66, wherein step (i) occurs at a weight hourly space velocity (WHSV) from 0.1 to 10 mass feed/mass catalyst/hour.

Clause 81. The method of clause 66, wherein prior to step (i) the method includes:
  contacting an aqueous hydrocarbon feedstock comprising water and one or more oxygenate with a condensation catalyst to produce a condensation product stream comprising $C_{4+}$ compounds, wherein the $C_{4+}$ compounds comprises a $C_{4+}$ alcohol, a $C_{4+}$ ketone, a $C_{4+}$ alkane, a $C_{4+}$ alkene, a $C_{5+}$ cycloalkane, a $C_{5+}$ cycloalkene, an aryl, or a fused aryl;
  fractionating the condensation product stream to separate a $C_{6-}$ stream from a $C_{7+}$ stream;
  recycling the $C_{6-}$ stream to the condensation catalyst;
  fractionating the $C_{7+}$ stream into a $C_{7-10}$ stream and a $C_{11+}$ stream, wherein the $C_{7-10}$ stream forms the mixed aromatic feed stream; and
  wherein at least a portion of the $C_{8+}$ stream bypasses the distillation column in step (iii) and is combined with the $C_8$ stream prior to entering the isomer-recovery process unit.

The invention claimed is:

1. A method for producing and separating a xylene isomer, the method comprising:
  (i) contacting a mixed aromatic feed stream comprising $C_{7+}$ aromatics with an aromatics processing catalyst to produce a product stream comprising an increased concentration of $C_8$ aromatics relative to the mixed aromatic feed stream, wherein the aromatics processing catalyst comprises a transalkylation catalyst, a dealkylation catalyst, a hydrocracking catalyst or a combination thereof;
  (ii) fractionating, using a distillation column, the product stream into a $C_{7-}$ stream and a $C_{8+}$ stream;
  (iii) fractionating, using a distillation column, at least a portion of the $C_{8+}$ stream into a $C_8$ stream and a $C_{9+}$ stream;
  (iv) subjecting at least a portion of the $C_8$ stream to an isomer-recovery process unit to produce a xylene isomer stream and a raffinate stream comprising non-recovered $C_8$ compounds; and
  (v) contacting the raffinate stream with an isomerization catalyst to produce an isomerization product stream, wherein the isomerization product stream comprises at least one xylene isomer,
  wherein at least a portion of the isomerization product stream is combined with the $C_8$ stream prior to entering the isomer-recovery process unit, and
  wherein at least a portion of the $C_{8+}$ stream bypasses the distillation column in step (iii) and is combined with the $C_8$ stream prior to entering the isomer-recovery process unit.

2. The method of claim 1, wherein the xylene isomer stream comprises para-xylene, ortho-xylene, or meta-xylene.

3. The method of claim 1, wherein prior to step (i) the method comprises:
  contacting an aqueous hydrocarbon feedstock comprising water and one or more oxygenate with a condensation catalyst to produce a condensation product stream comprising C4+ compounds, wherein the C4+ compounds comprise a $C_{4+}$ alcohol, a $C_{4+}$ ketone, a $C_{4+}$ alkane, a $C_{4+}$ alkene, a $C_{5+}$ cycloalkane, a $C_{5+}$ cycloalkene, an aryl, or a fused aryl;
  fractionating the condensation product stream to separate a $C_{6-}$ stream from a $C_{7+}$ stream;
  recycling the $C_{6-}$ stream to the condensation catalyst;
  fractionating the $C_{7+}$ stream into a $C_{7-10}$ stream and a $C_{11+}$ stream, wherein the $C_{7-10}$ stream forms the mixed aromatic feed stream.

4. The method of claim 1,
  wherein, based on the total weight of the mixed aromatic feed stream, the mixed aromatic feed stream comprises:
    from 0.1 wt % to 45 wt % olefins;
    from 0.1 wt % to 25 wt % naphthenes;
    from 0.1 wt % to 40 wt % naphtheno-olefins;
    phenols in an amount from 10 ppm to 10 wt %; and/or
    oxygenates in an amount from 10 ppm to 10 wt %.

5. The method of claim 1, wherein the mixed aromatic feed stream has a bromine number of at least 1 mg $Br_2$/g of the mixed aromatic feed to less than 100 mg $Br_2$/g of the mixed aromatic feed.

6. The method of claim 1, wherein the mixed aromatic feed stream comprises $C_{9-10}$ aromatics.

7. The method of claim 5, wherein the $C_{7-}$ stream is fed to a distillation column that fractionates the $C_{7-}$ stream into a $C_{6-}$ stream and a $C_7$ stream.

8. The method of claim 7, wherein at least a portion of the $C_7$ stream is recycled and combined with the mixed aromatic feed stream.

9. The method of claim 1, wherein the $C_{9+}$ stream is fed to a fourth distillation column that fractionates the $C_{9+}$ stream into a $C_{9-10}$ stream and a $C_{11+}$ stream, wherein the $C_{9-10}$ stream is recycled and combined with the mixed aromatic feed stream.

10. The method of claim 1,
  wherein at least a portion of the isomerization product stream is combined with the product stream produced from the aromatics processing catalyst in step (i).

11. The method of claim 10, wherein the method further comprises:
  fractionating the $C_{7-}$ stream into a $C_{6-}$ stream and a $C_7$ stream; and
  fractionating the $C_{9+}$ stream into a $C_{9-10}$ stream and a $C_{11+}$ stream, wherein the $C_7$ stream and the $C_{9-10}$ stream are recycled and combined with the mixed aromatic feed stream.

12. The method of claim 10, wherein the method further comprises:
  fractionating the $C_{7-}$ stream into a $C_{6-}$ stream and a $C_7$ stream; and
  fractionating the $C_{9+}$ stream into a $C_{9-10}$ stream and a $C_{11+}$ stream, wherein the $C_7$ stream is recycled and combined with the mixed aromatic feed stream and the $C_{9+}$ stream is recovered as a product.

13. The method of claim 1, wherein the isomer-recovery process unit comprises an adsorption unit or a crystallization unit.

14. The method of claim 1, wherein the aromatics processing catalyst comprises an acid catalyst, which comprises aluminosilicates, tungstated aluminosilicates, silica-alumina phosphates, aluminum phosphates, amorphous silica alumina, zirconia, sulfated zirconia, tungstated zirconia, tungsten carbide, molybdenum carbide, titania, acidic alumina, phosphated alumina, tungstated alumina, phosphated silica, tungstated silica, tungstated titania, tungstated phosphate, niobia, sulfated carbons, phosphated carbons, acidic resins, heteropolyacids, tungstated heteropolyacid, inorganic acids, or a combination thereof; and wherein the acid catalyst comprises a metal, which comprises Cu, Ag, Au, Pt, Ni, Fe, Co, Ru, Rh, Zn, Ga, In, Pd, Ir, Re, Mn, Cr, Mo, W, Sn, Os, alloys, or a combination thereof.

15. The method of claim 1, wherein step (i) occurs at a temperature from 200° C. to 600° C., a pressure from 100 psig to 1500 psig, or a weight hourly space velocity (WHSV) from 0.1 to 10 mass feed/mass catalyst/hour, or wherein step (i) comprises feeding hydrogen in an amount of at least 0.1 mol of hydrogen per mol of mixed aromatic feed.

* * * * *